United States Patent
Braun et al.

(10) Patent No.: US 10,769,741 B2
(45) Date of Patent: *Sep. 8, 2020

(54) EMERGENCY RESPONSE AUGMENTED REALITY-BASED NOTIFICATION

(71) Applicant: Emergency University, Inc., Emerald Hills, CA (US)

(72) Inventors: Odelia Braun, Emerald Hills, CA (US); Doron Braun, Emerald Hills, CA (US); Andrew Richard Johnston, Scotts Valley, CA (US)

(73) Assignee: Emergency University, Inc., Emerald Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/425,433

(22) Filed: May 29, 2019

(65) Prior Publication Data

US 2019/0279327 A1   Sep. 12, 2019

Related U.S. Application Data

(63) Continuation-in-part of application No. 15/085,492, filed on Mar. 30, 2016, now abandoned, which is a
(Continued)

(51) Int. Cl.
*G06Q 10/10* (2012.01)
*G06Q 30/02* (2012.01)
(Continued)

(52) U.S. Cl.
CPC ....... *G06Q 50/265* (2013.01); *G06F 19/3418* (2013.01); *G06Q 10/00* (2013.01);
(Continued)

(58) Field of Classification Search
CPC ...... G06Q 10/10; G06Q 50/265; G06Q 50/22; G06Q 10/00; G06Q 10/063112;
(Continued)

(56) References Cited

U.S. PATENT DOCUMENTS

| 5,228,449 A | 7/1993 | Christ et al. |
| 5,960,337 A | 9/1999 | Brewster et al. |

(Continued)

FOREIGN PATENT DOCUMENTS

| KR | 20060089975 A | 8/2006 |
| WO | 200225319 A2 | 3/2002 |
| WO | 2013142900 A1 | 10/2013 |

OTHER PUBLICATIONS

Acker, J.E., Implementation Strategies for Emergency Medical Services Within Stroke System of Care, American Stroke Association, Stroke, 2007;38:3097-3115, Originally published Oct. 29, 2007) (2007).

(Continued)

*Primary Examiner* — Jonathan P Ouellette
(74) *Attorney, Agent, or Firm* — Perkins Coie LLP; Michael Glenn

(57) ABSTRACT

Embodiments of the invention leverage mobile proliferation to enable laypersons to initiate a timely and effective emergency response in case of an emergency, such as a medical emergency, e.g. cardiac event. Mobile apps are made available as part of an organization's overall response plan and program, allowing bystanders of emergency events to easily initiate notifications, for example to trained responders, for example in their facility, in a timely manner commensurate with the type of emergency specific to their facility. More particularly, embodiments of the invention use mobile applications to provide augmented reality-based alerts and notifications, for example to certified first trainees to respond to the scene of the emergency.

43 Claims, 31 Drawing Sheets

Related U.S. Application Data continuation of application No. 14/269,030, filed on May 2, 2014, now Pat. No. 9,324,120.

(60) Provisional application No. 61/892,836, filed on Oct. 18, 2013, provisional application No. 61/832,691, filed on Jun. 7, 2013.

(51) Int. Cl.

| | | |
|---|---|---|
| *G06Q 40/08* | (2012.01) | |
| *G06Q 10/08* | (2012.01) | |
| *G06Q 50/26* | (2012.01) | |
| *G06Q 10/00* | (2012.01) | |
| *G06F 19/00* | (2018.01) | |
| *G06Q 10/06* | (2012.01) | |
| *H04W 4/021* | (2018.01) | |
| *H04W 4/60* | (2018.01) | |
| *H04W 4/90* | (2018.01) | |
| *H04W 4/02* | (2018.01) | |
| *G16H 40/67* | (2018.01) | |
| *G06Q 50/22* | (2018.01) | |
| *H04L 29/06* | (2006.01) | |

(52) U.S. Cl.
CPC ..... *G06Q 10/063112* (2013.01); *G06Q 10/10* (2013.01); *G16H 40/67* (2018.01); *H04W 4/021* (2013.01); *H04W 4/023* (2013.01); *H04W 4/60* (2018.02); *H04W 4/90* (2018.02); *G06Q 50/22* (2013.01); *H04L 65/608* (2013.01); *H04M 2250/10* (2013.01)

(58) Field of Classification Search
CPC ... G06F 19/3418; G16H 40/67; H04W 4/021; H04W 4/60; H04W 4/90; H04W 4/023; H04L 65/608; H04M 2250/10
USPC .................................................. 705/1.1–912
See application file for complete search history.

(56) References Cited

U.S. PATENT DOCUMENTS

| | | | |
|---|---|---|---|
| 7,048,185 B2 | 5/2006 | Hart | |
| 7,091,852 B2 | 8/2006 | Mason et al. | |
| 7,171,217 B2 | 1/2007 | Beuck | |
| 7,177,623 B2 | 2/2007 | Baldwin | |
| 7,289,029 B2 | 10/2007 | Medema et al. | |
| 7,607,014 B2 | 10/2009 | Larson et al. | |
| 7,793,850 B1 | 9/2010 | Ho et al. | |
| 7,922,073 B2 | 4/2011 | de la Huerga | |
| 8,095,403 B2 | 1/2012 | Price | |
| 8,185,623 B2 | 5/2012 | Lewis et al. | |
| 8,300,922 B1 | 10/2012 | Garvey, III | |
| 8,314,683 B2 | 11/2012 | Pfeffer | |
| 8,350,693 B2 | 1/2013 | McSheffrey et al. | |
| 8,401,514 B2 | 3/2013 | Ebdon et al. | |
| 8,526,910 B2 | 9/2013 | Messerly | |
| 9,324,120 B2 | 4/2016 | Braun | |
| 2002/0026266 A1 | 2/2002 | Montague | |
| 2003/0069648 A1 | 4/2003 | Douglas et al. | |
| 2003/0233252 A1 | 12/2003 | Haskell et al. | |
| 2005/0151642 A1 | 7/2005 | Tupler et al. | |
| 2005/0190053 A1 | 9/2005 | Dione | |
| 2005/0239477 A1 | 10/2005 | Kim et al. | |
| 2005/0242928 A1 | 11/2005 | Kirkeby et al. | |
| 2006/0293023 A1 | 12/2006 | Levitan | |
| 2007/0174438 A9 | 7/2007 | Johnson et al. | |
| 2009/0034414 A1 | 2/2009 | Schuette et al. | |
| 2009/0143046 A1 | 6/2009 | Smith | |
| 2009/0196234 A1 | 8/2009 | Kimbark et al. | |
| 2009/0284348 A1* | 11/2009 | Pfeffer ................. | G08B 25/006 340/7.3 |
| 2010/0057502 A1 | 3/2010 | Arguelles et al. | |
| 2010/0100510 A1 | 4/2010 | Balaban et al. | |
| 2011/0117878 A1 | 5/2011 | Barash et al. | |
| 2011/0130636 A1 | 6/2011 | Daniel et al. | |
| 2011/0151829 A1 | 6/2011 | Velusamy et al. | |
| 2012/0110373 A1 | 5/2012 | Müller et al. | |
| 2012/0218102 A1 | 8/2012 | Bivens et al. | |
| 2012/0232355 A1 | 9/2012 | Freeman | |
| 2012/0271370 A1 | 10/2012 | Hochhalter et al. | |
| 2013/0012151 A1 | 1/2013 | Hankins | |
| 2013/0040600 A1 | 2/2013 | Reitnour et al. | |
| 2013/0053063 A1 | 2/2013 | McSheffrey | |
| 2013/0116922 A1* | 5/2013 | Cai ...................... | G01C 21/206 701/515 |
| 2013/0241726 A1 | 9/2013 | Hunter et al. | |
| 2013/0252574 A1 | 9/2013 | Single | |
| 2014/0002241 A1 | 1/2014 | Elghazzawi et al. | |
| 2014/0211927 A1 | 7/2014 | Clawson et al. | |
| 2014/0365390 A1 | 12/2014 | Braun et al. | |
| 2016/0210581 A1 | 7/2016 | Braun et al. | |
| 2019/0208392 A1* | 7/2019 | Merjanian .......... | G06K 9/00671 |

OTHER PUBLICATIONS

George, Stephen M., et al., "DistressNet: A Wireless Ad Hoc and Sensor Network Architecture for Situation Management in Diaster Response", IEEE Communications Magazine, Mar. 2010) (Year 2010) 128-136.

Tierney, Kathleen J., "Implementing a Seismic Computerized Alert Network (Scan) for Southern California: Lessons and Guidance from the Literature on Warning Response and Warning Systems", University of Delaware, Disaster Research Center, Final Project Report #45, Nov. 30, 2000, pp. i-vi, 1-87, appendices I, II.

"Hot Spare—Wikipedia", May 18, 2013 (May 18, 2013), XP055656649, Retrieved from the Internet: URL: https://en.wikipedia.org/w/index.php?title=Hot_spare&oldid=555622534 [retrieved on Jan. 10, 2020].

* cited by examiner

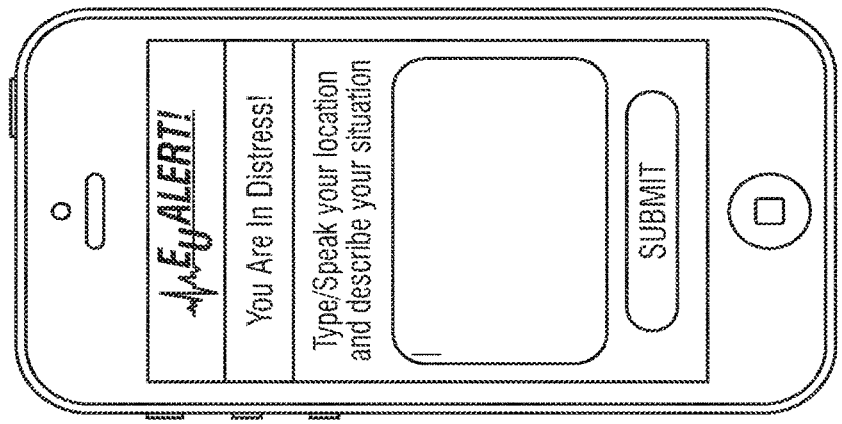
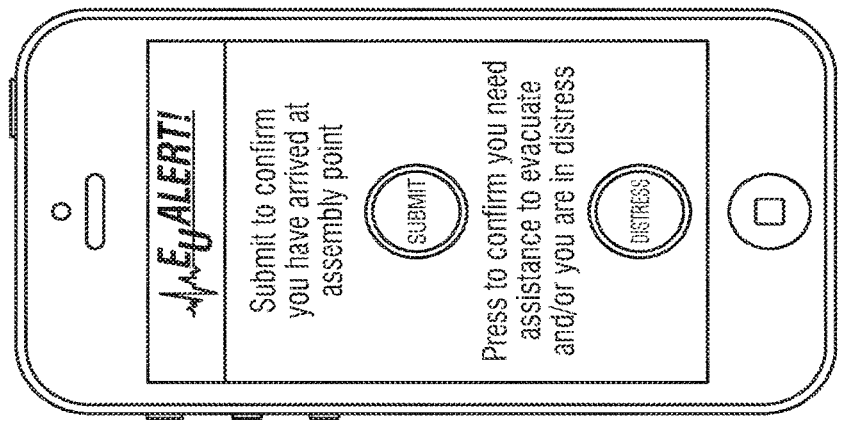
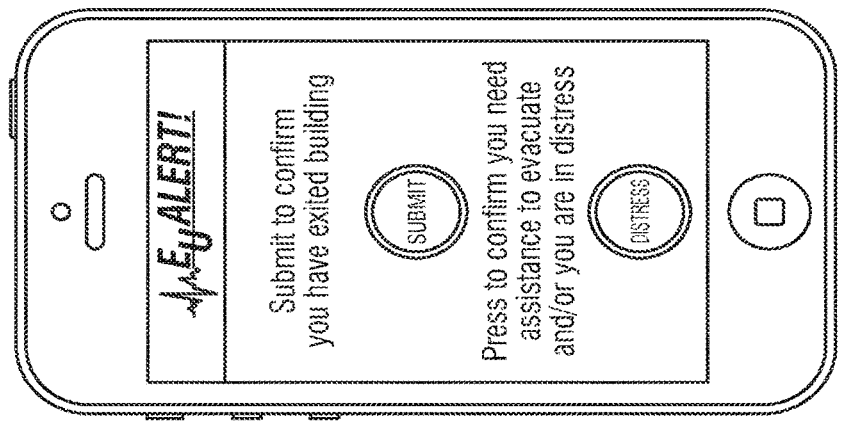
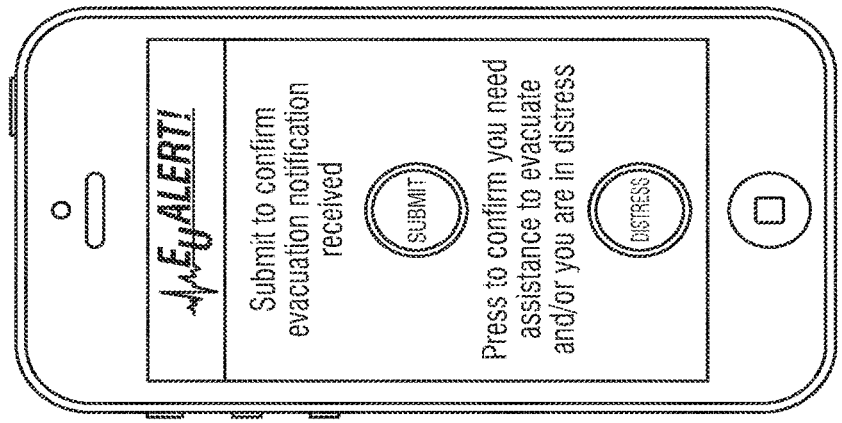

47. Who is immediately notified in a medical emergency? [Security]

48. Who contacts EMS in a medical emergency? [Responder]

49. Who meets EMS in a medical emergency? [Both]

50. What phone number is used to contact security? [7579837363]

51. What phone number is used to contact EMS (eg: 911, 9-911)? [9-911]

52. Which of the following is used to notify onsite personnel in a medical emergency? (Check all that apply.)
☑ Public address system
☑ Radio or walkie talkie
☐ Phone 53. What are the initial tasks to be performed in case of an emergency by the incident commander?
1. Shut off elevators
2. Shut down escalators
3. Lock down secure areas
4. Turn on emergency generator
5. Turn on emergency wifi system

[Previous] [Next]

Ⓐ  Ⓑ

Role-Based Tasks transmitted to responsible individual upon confirmation of receipt of notification of the emergency.

Within EUAlert, enter configuration mode & scan facility to establish horizontal and vertical planes attached to floors, walls, fixed objects

FIG. 20

EMERGENCY RESPONSE AUGMENTED REALITY-BASED NOTIFICATION

CROSS REFERENCE TO RELATED APPLICATIONS

This application is a continuation-in-part of U.S. patent application Ser. No. 15/085,492, filed Mar. 30, 2016, which is a continuation of U.S. patent application Ser. No. 14/269,030, filed May 2, 2014, now U.S. Pat. No. 9,324,120, which claims priority to U.S. provisional patent application Ser. No. 61/832,691, filed Jun. 7, 2013, and to U.S. provisional patent application Ser. No. 61/892,836, filed Oct. 18, 2013, each of which application is incorporated herein in its entirety by this reference thereto.

TECHNICAL FIELD

The invention relates to responding to emergencies. More particularly, the invention relates to providing augmented reality-based (AR-based) alerts to proximate, workforce or other personnel in the event of an emergency, such as a medical or other emergency.

BACKGROUND

Emergency response is a serious problem. Under such systems as 911, when seconds count, a responder is at least several minutes away. Consider, for example, cardiac arrest. Each Year 330,000 Americans experience sudden cardiac death, yet less than 5% of Americans receive CPR training annually. The majority of these trainees are health care professionals who work in controlled medical environments such as hospitals, ambulances, and clinics. However, the majority of cardiac arrests take place at work or in the home. While EMS systems have evolved to bring trained medical professionals to the scene of a medical emergency more rapidly, the optimal window for medical intervention in a cardiac arrest is often too narrow to allow for the timely transport of equipment and skills to the location of the victim.

The probability of surviving an out-of-hospital cardiac arrest is at least doubled for victims who receive bystander CPR. In addition, cardiac arrest victims who receive bystander CPR and the benefit of an automated external defibrillator (AED) that can deliver a shock to the heart within four minutes quadruple their survival with reports of survival between 34-70%.

However, victims receive the benefit of bystander CPR only 7-28% of the time and receive the combined benefit of bystander CPR and AED application only 2-3.4% of the time. While researchers and clinicians understand what elements are necessary to improve survival from cardiac arrest, it is as yet not possible to deliver these components to the cardiac arrest victim in a timely fashion.

A major problem in this regard lies in the fact that there is statistically a very small likelihood that a trained responder is present when a cardiac arrest occurs. The bystander, unfamiliar with the emergency medical response, most often does nothing, or merely calls emergency medical services (EMS), i.e. 911.

A sudden cardiac arrest (SCA) is an emotionally daunting event. As such, most laypersons are unwilling to perform unfamiliar tasks, such as AED and CPR, in public under these emotionally charged circumstances. The best EMS response times nationwide are greater than four minutes, and the average response time is between 8-12 minutes. Thus, trained personnel, and the appropriate equipment (AEDs), arrive at the victim's side too late to impact survival. This is best understood when one considers that EMS requires a minimum of an additional 2-4 minutes to process a call. EMS obtains information regarding responders and equipment voluntarily and is therefore an incomplete network of both trained responders and equipment. EMS has no way to ascertain the continued validity of the information initially provided, which experientially has been demonstrated to change by 20%/year. Further, EMS has no way to ascertain the operational status of the equipment because it does not maintain this information itself.

Additionally, EMS has no way to customize the information based on organizational structure, nor does it have the operational plans and protocols of different organizations in the community.

To address this issue, many workplaces have instituted internal emergency response plans and trained workplace personnel in CPR and AED. They have purchased AEDs to be placed at convenient locations throughout the workplace. However, the average number of trained personnel in the workforce averages 2-10% Therefore, victims still do not collapse near their trained responders.

The foregoing discussion considers a single type of emergency, i.e. a specific medical emergency. Yet, there are many types of emergencies that require prompt and, often, a skilled response. It would be advantageous to provide an approach that enables prompt notification to elicit early response to such emergencies.

SUMMARY

Embodiments of the invention leverage mobile proliferation to enable laypersons to initiate a timely and effective emergency response in case of an emergency, such as a medical emergency, e.g. cardiac event. Mobile applications (APPS) are made available as part of an organization's overall response plan and program, allowing bystanders of emergency events to easily initiate notification of, for example, trained responders, specific to their facility. More particularly, embodiments of the invention use mobile applications to provide AR-based alerts to workforce personnel, such as to certified first responders, to respond to the scene of the emergency. In the example of first responders, mobile applications also inform certified first responders of the nearest operational emergency equipment and can provide specific instructions to the certified first responders regarding the emergency and how best to respond.

BRIEF DESCRIPTION OF THE DRAWINGS

FIGS. 9A-9D are a series of screenshots showing a workforce evacuation notification sequence according to the invention;

FIG. 20 is a flow diagram showing the establishment of horizontal and vertical planes according to the invention;

DETAILED DESCRIPTION

Figure 1:
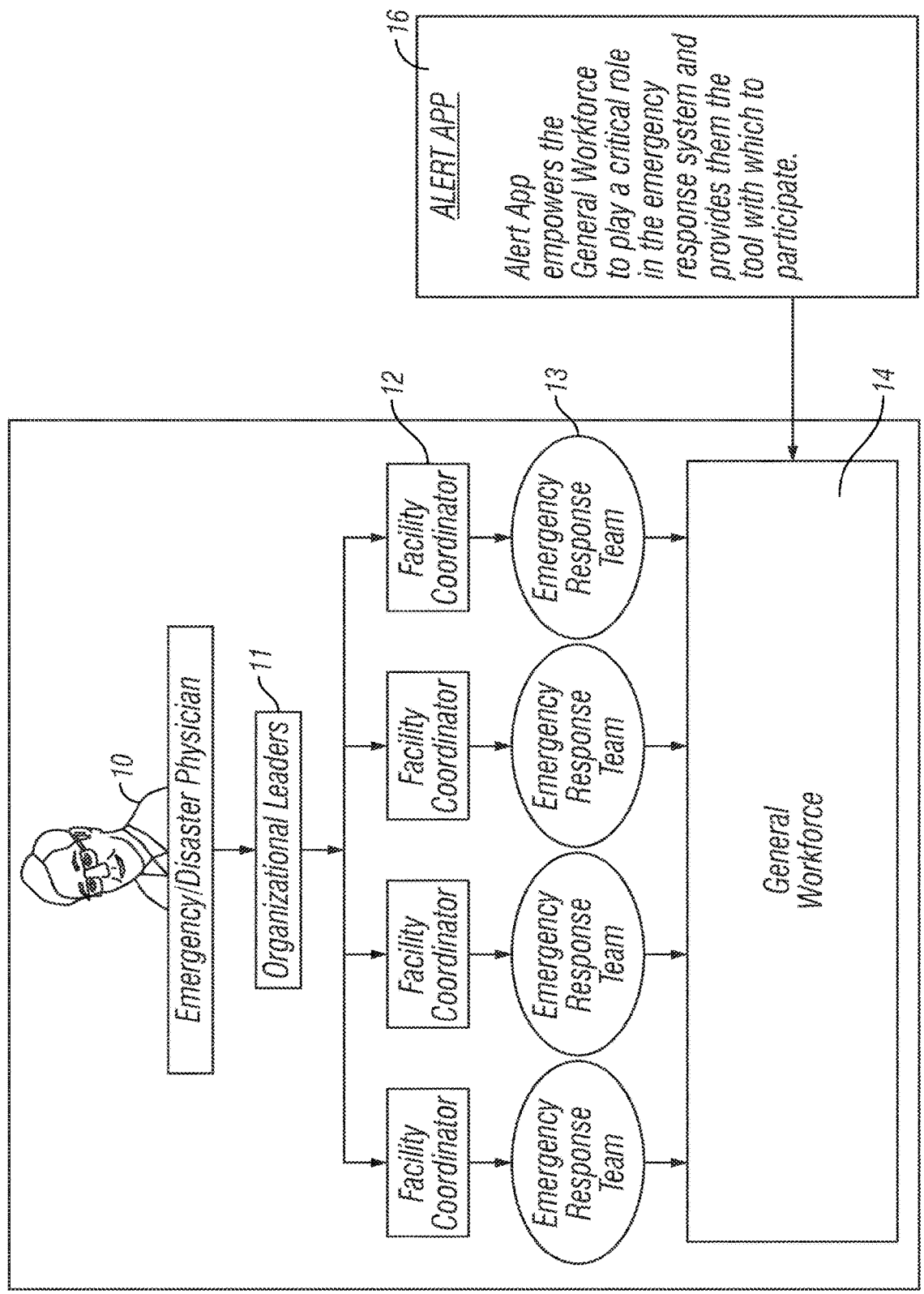
FIG. 1 is an organization diagram showing the participants in a tiered response system according to the invention.

Embodiments of the invention facilitate notification to workforce personnel in the event of an emergency, for example to prompt the arrival of trained personnel with the appropriate equipment to aid in an emergency, for example to assist a cardiac arrest victim or other emergency. In embodiments, individuals having no training can now alert trained co-workers in their workplace to respond immediately in an emergency, e.g. to the victim of cardiac arrest, via a mobile application that notifies all trained responders in the facility via text and email. This allows the untrained bystander to contribute in a meaningful way in an emergency while not requiring the bystander to perform an unfamiliar task in public under pressure. Importantly, while 911 can be included as part of the initial notification, the use of the 911 service is not required to obtain or send the initial notifications, thus saving important minutes.

Embodiments of the invention include a database that tracks the training and certification of all workplace personnel, as well as the date of their certification, and whether they have received special responder classes or other applicable training classes or certifications. Trained personnel are notified by the bystander in order, prioritized, for example, by the quality of their training and preparation, as defined by the most recent certification dates, and whether they have received a special responder class or other applicable training classes or certifications.

Those skilled in the art will appreciate that, while the invention is described in connection with trained responders and medical emergencies, embodiments of the invention apply generally to notifying and communicating with any set or subset of workforce personnel for any type of emergency. For example, application of the invention to workforce assembly and mustering are described in greater detail below.

In the case of a cardiac arrest response, the trainees are tracked by the completion of CPR, AED, and AED Responder online training modules, and their dates of completion. They are also tracked by the date they demonstrate skills competence in these classes, as verified by an instructor. Certification is awarded when both the online training modules and skills competence have been successfully completed. Re-certification is required every two years and each re-certification date is maintained in the system. Trainees are also tracked by the completion of the AED responder class, and they are awarded certification upon completion of this class.

The rules engine first looks to the closest facility, then prioritizes by the trainees who have current certification in AED Responder and CPR/AED. Next, it looks to trainees who have current certification in CPR/AED, but not AED Responder. Next, it looks to trainees who have previously been certified, but are not currently certified in CPR/AED. Then, it looks to trainees who have previously completed either CPR/AED skills or the online training programs. Those skilled in the art will appreciate that the order of prioritization may be changed and that some steps may be left out, while other steps may be added, all as appropriate and desired. Further, while this embodiment of the invention concerns medical emergencies and, in particular an SCA, those skilled in the art will appreciate that such rules and prioritization can be applied as appropriate to any emergency event in which the invention is used.

FIG. 1 is an organization diagram showing the participants in a tiered response system according to the invention. In embodiments of the invention, a four-tier emergency response system is established for organizations. Each tier of the emergency response system has its own roles and responsibilities. Training specific to each tier's responsibilities is provided, as are the equipment and tools necessary for each tier to fulfill their respective roles.

Organization-wide emergency policies and procedures are developed with the leaders of the organization 11, the first tier. The second tier of the system, each facility's program coordinator 12, develops a facility specific emergency response plan. The trained responders 13 form the third tier of the emergency response system, and the fourth tier is the general workforce 14 who is not trained and is targeted by a mobile application. An emergency/disaster physician 10 typically oversees the emergency response system in the case of medical emergencies.

Those skilled in the art will appreciate that the invention is not limited to medical emergencies and applies as well to other emergencies, such as might occur in the case of a fire, flood, storm, earthquake, terror attack, etc. A key feature of the invention is the bystander-initiated notification of an emergency for which a response by trained personnel is required and the automatic identification and notification of such responders on the basis of event-related rules, as well as prioritization of such notifications. This creates and ad hoc network for emergency response that is independent of public services, such as the 911 service. As such, there is no need to operate through an intermediary, such as a central dispatcher. In this way, precious time is saved. This is especially important in a cardiac arrest because the likelihood of survival decreases by 10% with each passing minute from the moment of collapse. It is estimated that on average, use of an internal notification system decreases the time to defibrillation from 10-12 minutes to 1-3 minutes. If the emergency is a wide-ranging event, where a central response system would be overburdened and, as such, subject to limited resources and degraded response times. Embodiments of the invention avoid such bottleneck. Nonetheless, embodiments of the invention are able to create an impromptu, tiered command structure through the application of rules and prioritization with regard to the communication of notifications. These rules define roles and assess abilities, locate equipment, and the like without the need for a central dispatch facility.

For example, with regard to non-medical emergencies, each company should have an emergency response plan. Such plans include the concept of who does what, in what instances, and when.

For example, at Tier one, incident command, one to three people are designated as the incident command, where two of the people are backups. The organization's Emergency Response Plan includes a list of initial tasks that should be immediately completed in case of specific emergencies, for example in a fire. The incident commander's initial responsibilities include for example, turning off elevators, escalators, shutting down secure areas, calling the Fire Marshall, calling the security team, etc.

Practically speaking, in a private sector emergency, incident commanders typically, have very little experience with managing emergencies and do not know what their initial tasks are. They somehow need to find their long neglected, dusty emergency response plan notebook, written by someone else, at some previous time, in a drawer somewhere.

In contrast thereto, with the herein disclosed alert APP, a bystander can click on, e.g. fire and the incident commander receives a text that lists all the initial tasks that he is charged with, and a link to his protocol or plan.

Tier 2 and, sometimes Tier 3, includes the emergency response team or floor wardens, which consists of a predetermined number of people per floor; and/or security, which is variable by company, i.e. different names are often used in the middle tier for similar function. At this level in the hierarchy, participants receive texts and/or emails that tell them exactly what equipment they should retrieve, where it is located, and directions to where they should station themselves to assist in the evacuation. Such notifications list the proper steps in evacuating personnel, e.g. links to additional immediately necessary information. Their responsibilities, tasks, and the equipment they need to retrieve information are described in their organization's emergency response policies and procedures, again in a notebook an unknown dusty drawer, and which no one reads, but for which they are responsible. In embodiments of the invention, the APP extracts the relevant task related information from the emergency response plan, which is pre-loaded into the database, and which is accessible by defined fields, and transmits this critical information to specific individuals who need it at the time they need it.

In appropriate emergencies, the general workforce receives instructions to evacuate, and directions to the nearest evacuation exist, as well as the location and directions to the assembly point located at a safe distance from their building or facility.

The individuals are pre-configured in the database as to their role, i.e. incident commander, emergency response team, security, general workforce, etc. The individuals receive instructions from their pre-existing emergency response plans (ERPs), and policies, procedures, and protocols according to their role. These instructions are taken directly from the company's emergency response policies, procedures, protocols and plans, all of which are documents that are stored in the database by templates and fields of unique texts, and which can be lifted into the notification text. This information comes directly from the database, is collected initially by management applications, and is selected for the particular user using the rules engine.

An important aspect of the invention concerns that fact that each participant in the emergency response system is enabled to communicate with each other person, and such communications are organized in tiers to implement a command structure spontaneously and in real time. Thus, roles are filled from a pool of candidates based upon their availability and also, for example, their proximity, skills, certification, etc. Information within the network of participants is routed, based upon the rules and prioritization, to the right person when it is needed. Thus, in addition to defining a tiered organizational structure in real time, the system provides instructions as well. In this way, each individual's role is reinforced, and each individual's skills are augmented. For example, the location of each participant in the emergency response system is known from the individual's profile information and/or from real time tracking information; each individual's skills and availability is known; and all emergency equipment in inventory is known as to its location, capabilities, and operational state.

In embodiments of the invention, a database and rules engine provide an information storage and routing facility, although in other embodiments of the invention such structure and knowledge need not be stored in a central server or cleared through a central dispatch facility. Rather, the initiation of an alert by a bystander propagates a series of notifications through a network of participants, for example, by use of an APP on their personal wireless device, where all rules and information is distributed, with pertinent rules for each individual on their device, as well as all profile information that is necessary to involve the individual appropriately in the tiered emergency response structure. In all embodiments of the invention, the mobile device can comprise, for example, a smartphone, such as an iPhone, tablet, watch, automotive device, aviation or nautical device, wearable device, such as Google Glass, or any other device that is capable of receiving transmissions.

Thus, in embodiments of the invention, the APP is used independently of a server, such as the rules engine and database. In such cases, the APP is subject to periodic synching with the database to ensure that the cached information stored in the APP remains current. Further, the database and rule engine can be periodically distributed to or cached on one or more of the handheld devices as a backup if the central system is not reachable during an emergency. Notifications are then sent directly, to the extent possible, from the bystander's phone.

In some embodiments of the invention, a more comprehensive user profile is collected at time of registration, and the user can inform the system of any skills, professional license, training, or equipment that they have and are willing to share, i.e. there may be people who were not trained by a specific organization; who are not known to be trained but are, in fact, trained; and/or have capabilities that would enable them to assist in an emergency.

In other embodiments of the invention, the APP is downloaded by workforce members, or even ordinary people who may or may not be part of an organization and who, as part of their user profile, potentially wish to share their medical information, i.e. potential patients and/or victims, so that they can personally initiate an alert, and indicate consent by a separate button "Share my medical information" with the trained responders to facilitate care. For example, a workforce member may be diabetic, and initiate the internal response system by selecting "share my information," in which case the responders would be notified that he is a diabetic and they could bring orange juice or sugar for a more rapid recovery. Other examples of the aspect of the invention include individuals who are allergic to certain foods, e.g. peanuts, or medications and who, upon feeling symptoms of an allergic reaction, could initiate a call for assistance that can also indicate, for example, the fact that the individual carries an EpiPen, which the responder could then find in the individual's purse, etc. Once found, this would allow the individual to be injected. Another example concerns someone who has a pacemaker or an internal defibrillator that they can tell is malfunctioning. In such case, they can send out a notification and receive immediate assistance. In the foregoing embodiments, rules are applied to identify an individual having known disabilities, as specified during the individual's registration, and a pre-configured distress signal is issued during, for example, an evacuation, with specific instructions for the trained responder, and directions to the nearest appropriate equipment based upon the disability, to assist the individual with equipment necessary to ensure that they are able to evacuate the individual.

In an embodiment of the invention, the general workforce is provided an overview of the organization's emergency response program. The overview provides the workforce with the knowledge that the organization has emergency response resources in its facilities, that there are trained responders, that there is an internal emergency response system, and that they play an important role in the system, i.e. to activate the system to bring trained responders to the scene of the emergency.

The emergency response program can pertain to a building, a campus, a town, or any other facility or organization. The program can include, for example, predetermined assembly areas at which individuals are to gather in the event of an emergency. Embodiments of the invention allow individuals to be tracked and located, or to send out distress messages. In this way, those individuals who did not successfully escape can be assisted.

For example, upon notification of the need to evacuate and instructions and/or directions on where their closest evacuation point and assembly area is located, a member of the general workforce, is provided with three successive buttons that appear on their APP:

First, a button is provided that instructs the member: "Press to confirm that you have received the evacuation notification;"

Next, a button is provided that instructs the member: "Press to confirm that you have evacuated out of the building;" and Next, a button is provided that instructs the member: "Press to confirm that you have reached the assembly area."

A button stays on the screen that instructs the member: "Press to indicate that you are having difficulties evacuating," and a text field is provided to allow the participant to tell Incident Command (IC) what problems they are having and where they are located.

A report is constantly updated based on individuals confirming their evacuation, or lack thereof. The report is available to the IC and distributable by regions to the responsible ERT or security teams. Ideally, in companies that have security upon entering the building, the initial list of individuals inside in the structure is updated with those that have successfully evacuated, and special alerts are sent to ICs and ERT/security for individuals who are having difficulty evacuating and need assistance.

The mobile application ("APP") 16 empowers lay bystanders to play a critical yet simple role in the organization's emergency response system and provides them the tool with which to participate. The mobile application allows the bystander to initiate the facility's emergency response plan more rapidly by yelling out for help in the manner described in the emergency response plan, such as yelling out for help or using the nearest squawk box. Next, the APP instructs the lay bystander to notify trained workplace personnel via the mobile APP. Next, the APP instructs the lay bystander to initiate a call to 911, or the APP directly calls 911 by presenting the user with a button that indicates "Press to call 911." Once the button is pressed, the APP opens the phone function and places the call. The mobile APP continues to follow the originally prescribed emergency response plan but facilitates the more rapid arrival of trained responders. The mobile APP also provides a mechanism with which to simulate, for example, an SCA, with its drill function.

Medical Emergencies—Emergency Response Notification System

Figure 2:
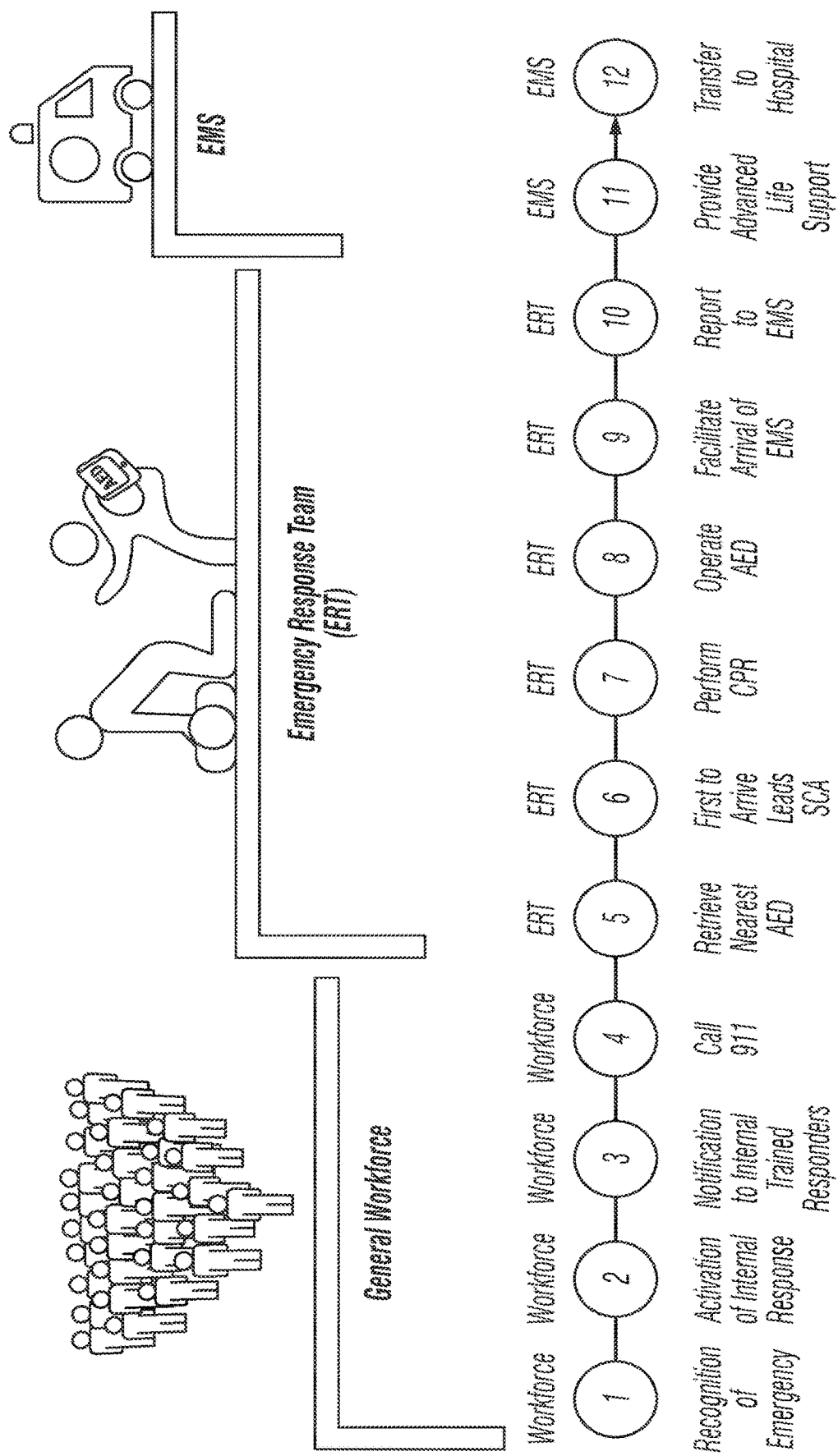
FIG. 2 is a flow diagram a medical emergency response model according to the invention.

FIG. 2 is a flow diagram a medical emergency response model according to the invention, in which the relationship between the general workforce, emergency response team and emergency medical services is shown. The flow in this model is discussed in detail below.

Figure 3:
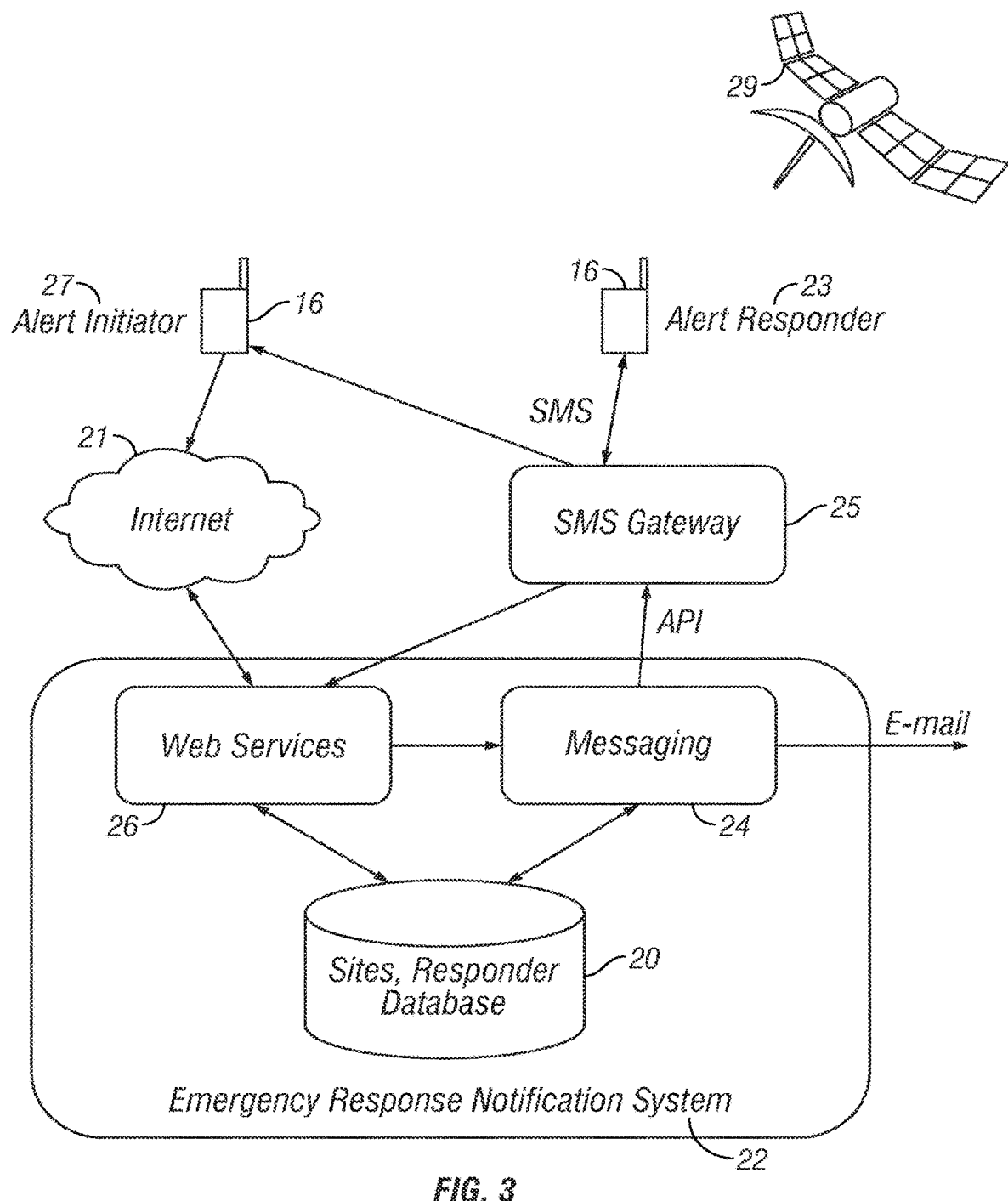
FIG. 3 is a block schematic diagram showing the main components of an emergency response notification system according to the invention.

FIG. 3 is a block schematic diagram showing the main components of an emergency response notification system according to the invention. These components include a database 20 that stores data acquired through management applications; a rules engine 22, including a learning management system ("LMS") that acquires and hierarchically stores raw data and that analyzes the data based on rules; a multi-mode, multi-dimensional communications, and two-way messaging and communication system 24, including emails, an SMS gateway 25, telephone and intelligent communications to provide progressive levels of intelligence, analyzed information, and compiled information that is dynamically driven by the rules engine, and including a mechanism for sending and receiving both human-to-human and technology generated intelligence, e.g. two-way communications and content between system participants, such as an alert initiator 27 and an alert responder 23; Web services 26 which communicate via the Internet 21, including business logic that performs functions directly on the database, initiates communications, provides analysis, and compiles reports; a mobile application 16 that provides an access point to the system and/or user interface; and geolocation capabilities 29.

Data stored in the database includes, for example:
1. Name of all individuals who have downloaded the APP, including their organization, their specific facility (location), their email address; and a cell phone number.
2. Name of all trained responders, including their organization, their specific facility (location), their email address;

a cell phone number, and the date of their most recent certifications, e.g. CPR/AED certification, AED responder certification, first aid certification, and the date of their most recent training, if they are not certified. Such information can also include the responder's role within a tiered emergency response organization and the specific emergency type for which they are to receive notification.
3. Location of emergency equipment, such as AEDs by organization, facility, address, location in facility, e.g. floor, and specific description of location, such as 9th floor elevator South, and GPS coordinates; date of last successful maintenance; and date of expiration for critical equipment, components, supplies, and medication that require routine replacement due to their age and/or expiration date.
4. Location of first aid, medical kits, oxygen, blood borne pathogen (BBP) kits by organization, facility, address, location in facility, e.g. floor, and specific description of location, such as 9th floor elevator South, and GPS coordinates; date of last successful maintenance; and date of expiration for supplies, equipment, and critical equipment, components, supplies, and medication that require routine replacement due to their age and/or expiration date.
5. Location of event initiated by APP by address, specific descriptive location, and, GPS.
6. Name(s) of designated Incident Control Commander(s) (IC), including their organization; their specific facility, address, GPS (location); email address; cell phone; and competence level, e.g. they can they make secondary decisions to initiate variable protocols and/or rely on preconfigured content, based on experience, training, using rules.
7. Name of designated Team Leaders, Security (Modified structures/designations) (TL), including their organization; their specific facility, address GPS (location); email address; cell phone; date of most recent CPR/AED certification; date of most recent AED Responder certification; date of most recent First Aid certification; date of most recent Evacuation Leadership training, or other pre-configured training requirements; date of most recent Incident Command (or other relevant) training; duration of service; and previous experience.
8. Name of all workforce personnel (WF), including their organization; their specific facility, address, GPS (location); email address; and cell phone.
9. Location of other Medical Emergency Equipment First Aid, Medical Kits, Oxygen, BBP kits, and other relevant supplies and/or equipment, including by organization; by facility; by address; by location in facility, e.g. floor, and specific description of location, such as 9th floor elevator South; by GPS coordinates; date of last successful maintenance; and date of pad and battery, medication expiration, AED's or other medical equipment or perishable supplies.
10. Location of non-emergency equipment and emergency equipment, such as fire extinguishers, evacuation equipment for personnel with disabilities, radios, walkie talkies, megaphones, vests, flags, etc., including by organization; by facility; by address; by location in facility, e.g. floor, and specific description of location, such as 9th floor elevator South; by GPS coordinates; and date of last successful maintenance.
11. Geo-location of boundaries of facility.
12. Geo-location of assembly area.
13. Dynamically generated geo-mapping and/or other technology for location of cell phones of workforce during emergency.
14. Comparison of security data of personnel location vs. confirmed evacuees and/or location of cell phones of workforce during emergency.

Rules

Rules can be implemented based on a pre-configured designation or they can be implemented dynamically.

Pre-configured rules are, for example, when an individual registers for the APP in the Boston Facility, an emergency notification is initiated in the Boston Facility and the database sends notifications to trained responders in the Boston facility, along with instructions about the location and operational status of AEDs in the Boston facility.

Dynamic rules are, for example, where the individual who is registered in Boston initiates an alert while in Maryland, as determined by GPS and address location applications, and the rules engine modifies its search dynamically for equipment and responders based on the individual's actual location. In this case, location can be accomplished by a coordinate mapping of the facility interpreted into addresses using GPS and address location applications, where the rules engine modifies its search for equipment and responders based on the individual's actual location.

Further, such rules can include the individual's role within a tiered organizational structure. In such case, the rules establish appropriate routing and chain-of-command to establish an ad hoc emergency response organization in real time.

For example, if the primary Incident Commander does not respond to the initial notification because, for example, he is out of town at a conference or sick, the rules engine notifies the first back-up incident commander and, if no response is received, then contacts the next back-up incident commander. The individual who first confirms IC notification receives a follow up text and/or email with an initial task list to perform and links to additional information that may be needed.

Organizations designate certain individuals as their ERT members or floor wardens and provide training to them. It is not known which of these workers are available on the day and time they are needed. The rules engine continues to search for appropriate responders, prioritized by training, experience, and location based on pre-configured data. As each potential responder confirms receipt, the responder is provided with the next series of tasks that needs to be performed on a per floor or per facility basis. For example, if the assignment to assist in the evacuation of the general workforce, then the first responder to confirm is sent to the primary exit door on the floor to shuttle the workforce out the appropriate exit door; the next responder is sent to the appropriate evacuation door from the building to continue exiting the workforce from the building; the third responder is located at the ground level to shuttle the workforce out of the building; and a fourth responder leads the evacuated workforce to the assembly area, etc. Security can be sent to assist distress calls that are routed through incident command (IC).

Process Flow

Figure 4:
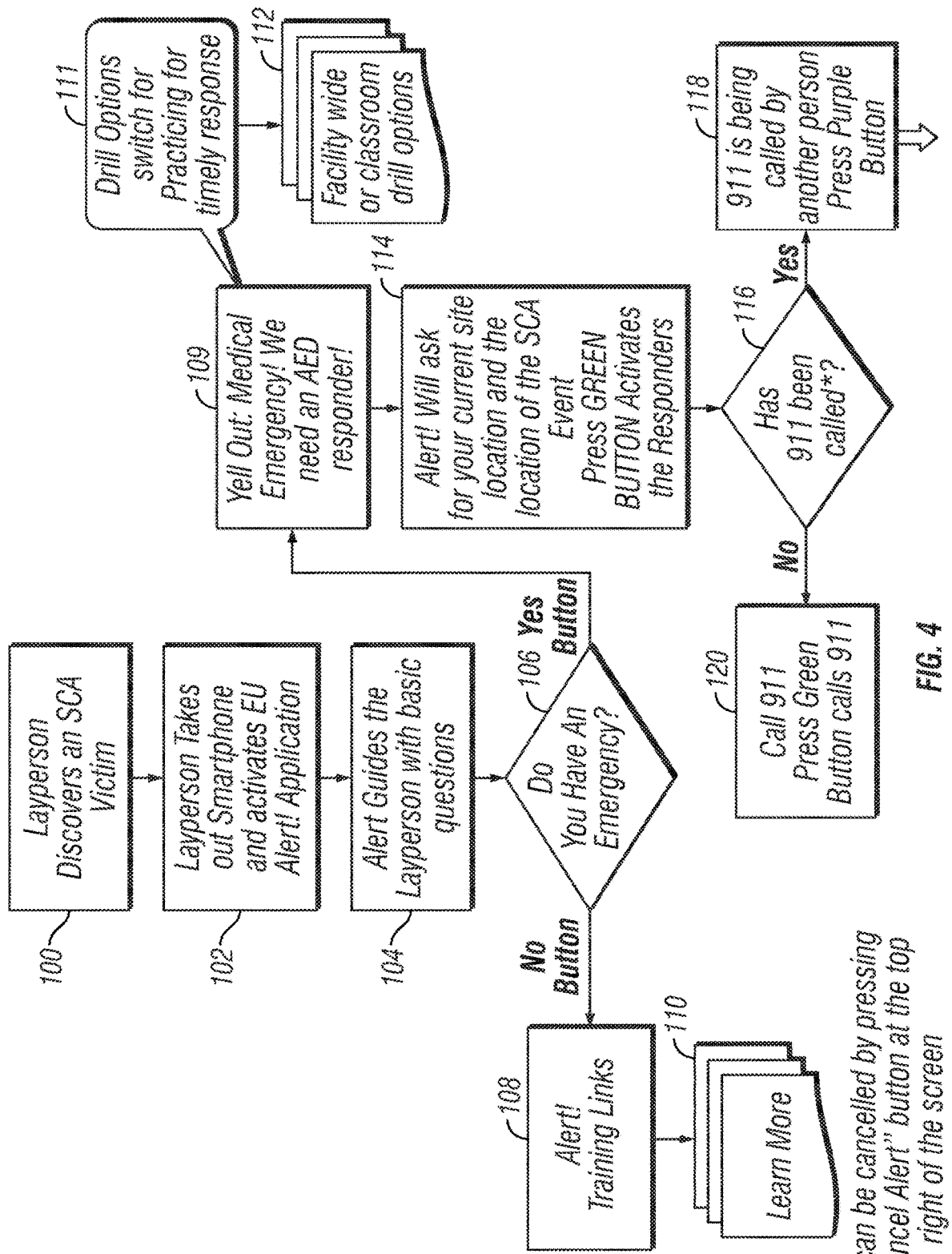
FIG. 4 is a flow diagram that shows a sequence of activities/communications in a medical emergency (ME) according to the invention.

FIG. 4 is a flow diagram that shows a sequence of activities/communications in a medical emergency (ME) according to the invention. Those skilled in the art will appreciate that the invention is readily applicable to other types of emergency.

As shown in FIG. 4, a bystander of an ME (100), in this case an SCA, initiates the emergency response notification system via a mobile application (102) by accessing and using the APP on a phone, tablet, etc. The bystander communicates with the APP and can enter the specific location of the ME within the facility, e.g. 3rd floor bathroom, by any form of information entry, such as typing, voice, etc.

As discussed above, the APP exchanges information via a communication system and Web service to access and interact with a rules engine and database. Information that is input by the bystander, e.g. via a cellular service, WIFI, and/or other system, is transmitted via the Web service to the rules engine and database.

In embodiments of the invention, a secondary screen displays, for example, a drop down or other menu that allows the bystander to select, for example the type of medical emergency, e.g. SCA. The selection of pre-configured types of medical emergencies shown on the display provides the bystander with a text description of each medical emergency, and thus facilitates an early assessment of the situation.

In embodiments of the invention, the bystander can also place a call to a service, such as 911, by calling 911 directly from the APP. As discussed above, the APP exchanges information via a communication system to access and, to the extent possible, interact with the 911 service. Where supported by the 911 service, information that is input by the bystander, e.g. via a cellular service, WIFI, and/or other system, is transmitted to the 911 service.

Responsive to the notification, the bystander of the ME receives an optional instruction to initiate first aid or resuscitation or other assistance as specified on the APP (104).

The APP receives a message that asks the bystander if there is an emergency (106). In this case there is an emergency, an SCA, as noted above. If the bystander is seeking information, but not providing notification of an emergency, the bystander can select the "No" button on the APP, in which case the bystander is provided with training links, (108) and can choose, as well, to receive further information in connection with such training (110).

In the bystander selects the "Yes" button on the APP, indicating that there is an emergency, the bystander may be alerted to yell out than an ME has occurred (109), e.g. "Medical emergency, we need an AED responder!" Embodiments of the invention contemplate using the system for preparedness training. Thus, the APP provides a drill options switch (111) for executing practice sessions. The scope of the drills can be established as desired (112), e.g. facility-wide or classroom drills. Drills can be coded to include only designated individuals, i.e. those in a specific class; or they can be non-coded, in which case all of the responders in the facility are notified of the drill.

In this example above, the ME is not a drill and the APP provides a simple dialog to the bystander to provide location information to the system such that trained responders can be located (114). Responsive thereto, the Web service runs a rule-driven query of rules engine and database that compares the location of event to that of a nearest facility having trained responders. The system locates nearest trained responders in the facility and prioritizes notification of the trained responders by applying rules that determine the level and type of training and competence required of the trained responder, as well as the proximity of the trained responder to the event. The system also locates the nearest appropriate equipment for the ME, such as AEDs and other medical equipment in the case of an SCA. The location of such equipment is prioritized by rules that evaluate the proximity of the equipment to the event, as well as the operational status of the equipment, e.g. if it has been recently serviced and is operable.

The bystander is also asked if the 911 service has been called (116). If the bystander responds with "Yes," then the bystander is asked if the 911 service is being called by a person other than the bystander (118), e.g. if "Yes," press the purple button. If the bystander responds with "No," the 911 service has not been called then the bystander is instructed to call the 911 service (120), e.g. press the green button to call the 911 service and proceed to the next screen.

Responsive thereto, a message containing specific information is sent to selected trained responders. In such case, the rules engine and database generate the message and the specific location of event within the facility is communicated to the selected trained responders with instructions to respond, prioritized by the trained responder's training, competency, and proximity rules. Embodiments of the invention also send the cell phone number of the bystander to the trained responder.

One or more messages are sent to the bystander indicating how many trained responders have been notified, e.g. to provide the bystander with peace of mind. In this case, the rules engine and database generate the message and the communications system sends the message to the bystander.

If no responders are available, a message sent to the bystander identifying the location of the nearest appropriate equipment, e.g. AEDs, prioritized by functionality rules. In this case, the rules engine and database generate the message and the communications system sends the message to the bystander.

The trained responders respond to the alert text with a confirmation message that communicates to the database via Web service indicating that they are responding. The message generates the geo-location of the trained responder.

One or more additional messages are sent to the bystander. Thus, as each trained responder responds to the alert, indicating whether the trained responder is coming or not coming to assist, the bystander receives such messages, e.g. for the bystander's peace of mind and to indicate that help is on the way. In such case, the rules engine and database generate the message and the communications system sends the message to the bystander.

One or more additional messages are sent to the trained responders. After the trained responders respond to the alert indicating they are coming to assist, the en route trained responders receive a message containing the location of the nearest operational emergency equipment, such as AEDs. In such case, the rules engine and database generate a message indicating the location of nearest functioning emergency equipment and the communications system sends the message indicating the location of nearest operational emergency equipment to trained responders who are en route.

In embodiments of the invention, the bystander records the time of arrival of the first trained responder via the APP, which then uses the Web service to record such data in the database. The bystander also records the time that emergency equipment and supplies are provided via the APP, which again uses the Web service to record such data in the database. Further, the bystander also records such other events as EMS arrival via the APP, which again uses the Web service to record such data in the database.

Embodiments of the invention provide emergency response data tracking, which documents the elapsed time from collapse to arrival of a first responder.

Embodiments of the invention allow the bystander to cancel the alert (as discussed above).

Embodiments of the invention allow a trained responder to communicate to bystander that they are on the way to provide assistance. As well, responders can communicate with each other, for example, where an impromptu, tiered emergency response is established to manage the response effort.

Database

All communications are logged in the database, and there is a report for each incident. Aggregate reports can be generated across multiple incidents. Information captured in the database includes, for example:
1. Date, time, and GPS location of the alert;
2. Who initiated the alert, by cell phone and GPS location;
3. Who is notified of the alert, by cell phone number;
4. Date and time of the notification;
5. Who responds to the notification, by cell phone number and GPS location;
6. Date and time that emergency equipment location information is sent to each responder via the communication system;
7. Date and time of notification of responding trained responder and geo-location of the trained responder at the time the confirming notification is sent;
8. Date and time of arrival of the first trained responder;
9. Date and time that the emergency equipment is placed in use, e.g. when an AED is attached;
10. Date and time of EMS arrival;
11. Date and time of alert and type of emergency;
12. Who initiated alert by cell phone;
13. Date and time that each IC was notified and confirmed notification;
14. Date and time that each TL notified and confirmed notification;
15. Date and time that each WF notified;
16. Date and time each IC, TL, and/or WF responded that they received initial notification;
17. Date and time that each WF confirmed notification received, successful evacuation, and successfully reached assembly area is confirmed;
18. Date and time and GPS of all "failure to evacuate" or "distress" messages;
19. Date and time and content of each ongoing communication by text between IC, TL, and/or WF and content of text and/or email communication; and
20. Date and time of EMS, fire, and/or police arrival by IC.

Sequence of Operations

Figure 5:
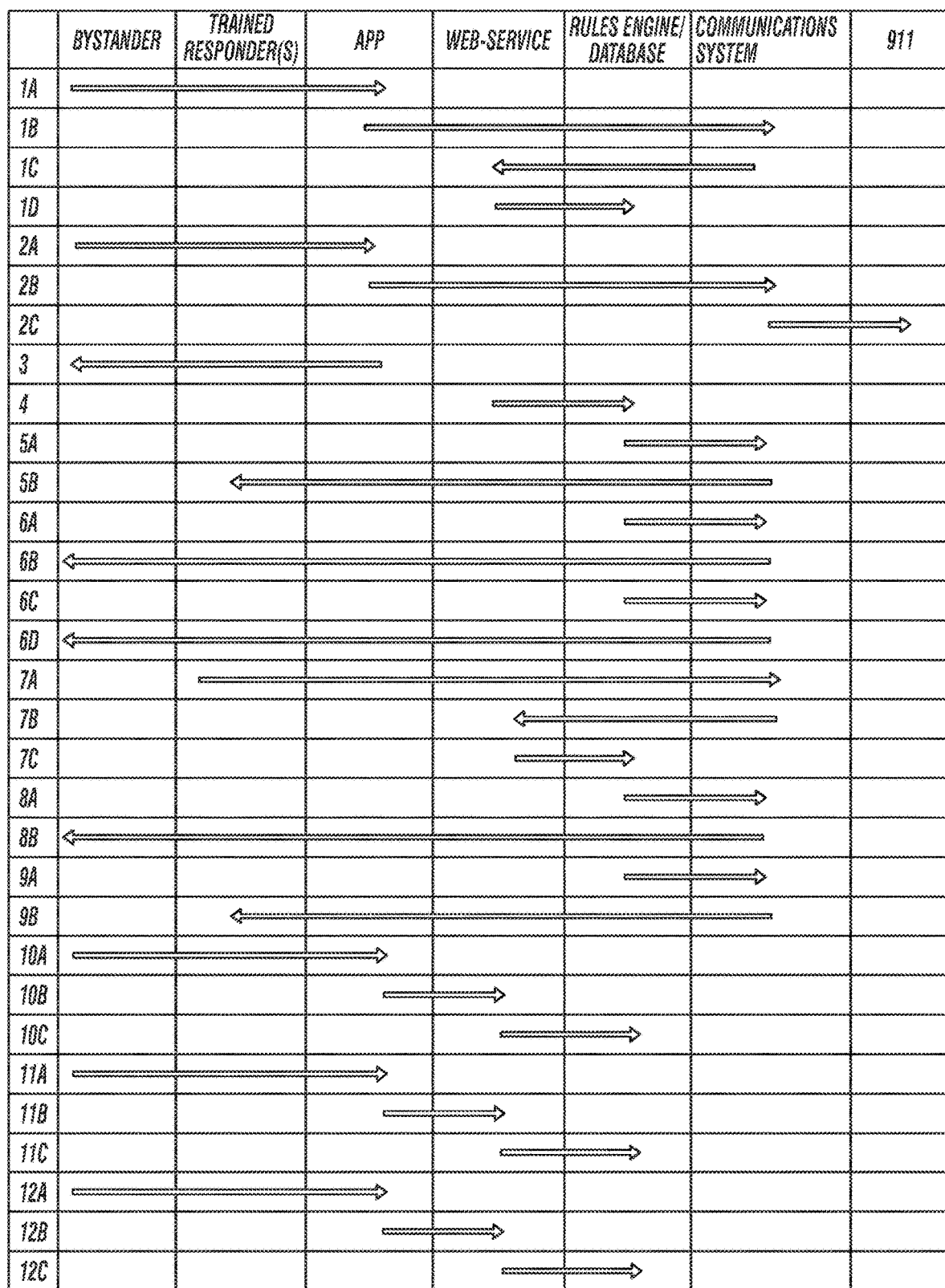
FIG. 5 is a flow diagram showing the sequence of operations during an emergency event according to the invention.

The foregoing is illustrated in FIG. 5, which is a flow diagram showing the sequence of operations during an emergency event according to the invention. In FIG. 5:

Step 1. Bystander of emergency, such as a medical emergency (ME), initiates emergency response notification system via mobile application ("APP"):
  1A: Bystander to APP-bystander of ME emergency initiates emergency response notification system via APP by accessing and using App on phone, tablet, etc.; bystander communicates (type/vocal input) to APP the specific location within the facility, e.g. 3rd floor bathroom); and
  1B: APP to communication system;
  1C: Communication system to Web service; and
  1D: Web service to rules engine/database—Data inputted by bystander, via cellular service, WIFI, etc., transmitted via Web service to rules engine/database.

Step 2. Bystander to 911—bystander of ME calls 911 directly from APP:
  2A: Bystander to APP;
  2B: APP to communication system; and
  2C: Communication system to 911;

Step 3. App to bystander—bystander of ME receives optional instruction to initiate first aid or resuscitation or other assistance as specified on the APP.

Step 4. Web service to rules engine/database—Web service runs rule-driven query of rules engine/database. This query includes:
  a. Comparing location of event to nearest facility having trained responders;
  b. Locating nearest trained responders in facility;
  c. Prioritizing notification of the trained responders by rules that determine the level and type of training, competence, proximity;
  d. Locating nearest emergency equipment, e.g. AEDs/medical equipment; and
  e. Prioritizing by rules that evaluate proximity to the event, and emergency equipment functionality.

Step 5. Message containing specific information sent to select trained responders:
  5A: Rules engine/database to communications system—Rules engine/database generates message; and
  5B Communications system to trained responders—Communications system communicates the following information to selected trained responders: The specific location of event within the facility with instructions to respond prioritized by trained responder training, competency and proximity rules.

Step 6. Message sent to bystander informing them how many trained responders have been notified):
  6A: Rules engine/database to communications system—Rules engine/database generates message; and
  6B: Communications system to bystander—Communications system sends message to bystander.
  If no responders are available, a message is sent to bystander informing the bystander of the location of the nearest emergency equipment prioritized by functionality rules:
  6C: Rules engine/database to communications system—Rules engine/database generates message; and
  6D: Communications system to bystander—Communications system sends message to bystander.

Step 7. Trained responder responds—Trained responders respond to the alert text with a confirmation message that communicates to database via the Web service indicating that they are responding. Message generates geo-location of the trained responder:
  7A: Trained responder to communication system;
  7B: Communication system to Web service; and
  7C: Web service to rules engine/database.

Step 8. Messages sent to bystander—As each trained responder responds to the alert, indicating that the trained responder is coming or not coming to assist, the bystander receives messages:
  8A: Rules engine/database to communications system—Rules engine/database generates message; and
  8B: Communications system to bystander—Communications system sends message to bystander.

Step 9. Messages sent to trained responders—After a trained responder responds to the alert indicating they are on the way the en route trained responders receive a message containing location of nearest operational emergency equipment:
  9A: Rules engine/database to communications system—Rules engine/database generates message indicating location of nearest functioning emergency equipment; and 9B: Communications system to trained responders—Communications system sends a message indicating the location of nearest operational emergency equipment trained responders who are en route.

Step 10. Bystander to APP—bystander records time of arrival of first trained responder via the APP which uses the Web service to record data in database:
10A: Bystander to APP;
10B: APP to Web service; and
10C: Web service to database.

Step 11. Bystander to APP—bystander records time that emergency equipment and supplies re provided via the APP which uses Web service to record data in the database:
11A: Bystander to APP;
11 B: APP to Web service; and
11C: Web service to database.

Step 12. Bystander to APP—bystander records EMS arrival via APP which uses the Web service to record data in the database:
12A: Bystander to APP;
12B: APP to Web service; and
12C: Web service to database.

Content

In embodiments of the invention, content that is communicated amongst the participants can include, for example, specific written instructions on actions to perform; graphic representations, i.e. of actions to perform, video, voice, and graphics; use of voice commands/technology, such as SIM to provide instructions and/or content; and multi-lingual capabilities. For example, this invention can be used with any language including, for example, Chinese, Japanese, etc. with which the database is compatible.

In embodiments of the invention, participants receive content, based upon their role, that includes:

ICs: Based on company-established level of responsibility, company-based emergency response policies and procedures, and other instructive company established documents and protocols:
  Initial procedures, e.g. turn off elevators and escalators, lock certain doors, contact specific authorities inside and outside of company;
  Option to initiate variable protocols based by type of emergency, including primary and secondary emergencies, medical emergencies, non-medical, emergencies, etc.; and
  Ongoing communications.

TLs or other designees, such as security: Based on company [established level of responsibility, company-based emergency response policies and procedures of company, and other instructive company established documents and protocols:
  Initial procedures, e.g. get radio, vest, megaphone, and/or flag, and go to pre-assigned location to assist evacuation; and
  Ongoing communications.

WF: Based on emergency response policies and procedures of company and level of complexity (described below):
  Simple notification text instruction to evacuate and location of assembly area;
  Text indicating location of nearest exit based on their pre-configured location and assembly area;
  Graphic of evacuation route for their pre-configured location and assembly area;
  GPS or other technology driven instructions to nearest exit and to assembly point based on their dynamic location; and
  Bluetooth or wireless or other frequency transmitter driven instructions to nearest exit and to assembly point.

Drill Functions

As discussed above, drill functions can be performed to prepare participants for an emergency. Drill codes allow selection of an ad hoc group of participants, independent of organization or geographic boundaries. At the start of a drill, all participants are given a shared code, which each person enters at about the same time into his handheld device. This code therefore defines the group of participants. Drill codes automatically expire after a fixed time, e.g. the duration of a drill, so that they can re-used in the future. When a drill incident is initiated, only the participants in the pool with valid, unexpired drill codes are alerted. Using drill codes during responder classes allows the emergency response system to be used across organizational barriers or geography.

A drill simulates an emergency and helps assess the adequacy of emergency response in the facility and/or organization and to allow repetitive practice, which enhances the quality and reduces the time to carry out the response with increased familiarity. The instructor for the drill enters drill code as initiator of the drill. Students, responders, and personnel attending the class enter drill code as responders. Only those individuals who have entered the drill code receive the communications during the drill. All messaging begins with a notification that is received via the APP, such as MEDICAL DRILL/EMERGENCY DRILL.

Spontaneous drills, i.e. drills that do not have drill codes, may also be held to test the system and response abilities of a facility and to empower the workforce by practicing for an emergency. In such cases, all responders receive all communications and all messaging begins with a notification that is received via the APP, such as MEDICAL DRILL/EMERGENCY DRILL. The instructor or other authorized person can cancel the alert at any time via the APP.

Sudden Cardiac Arrest ("SCA") Emergency Response Notification System

Figure 6:
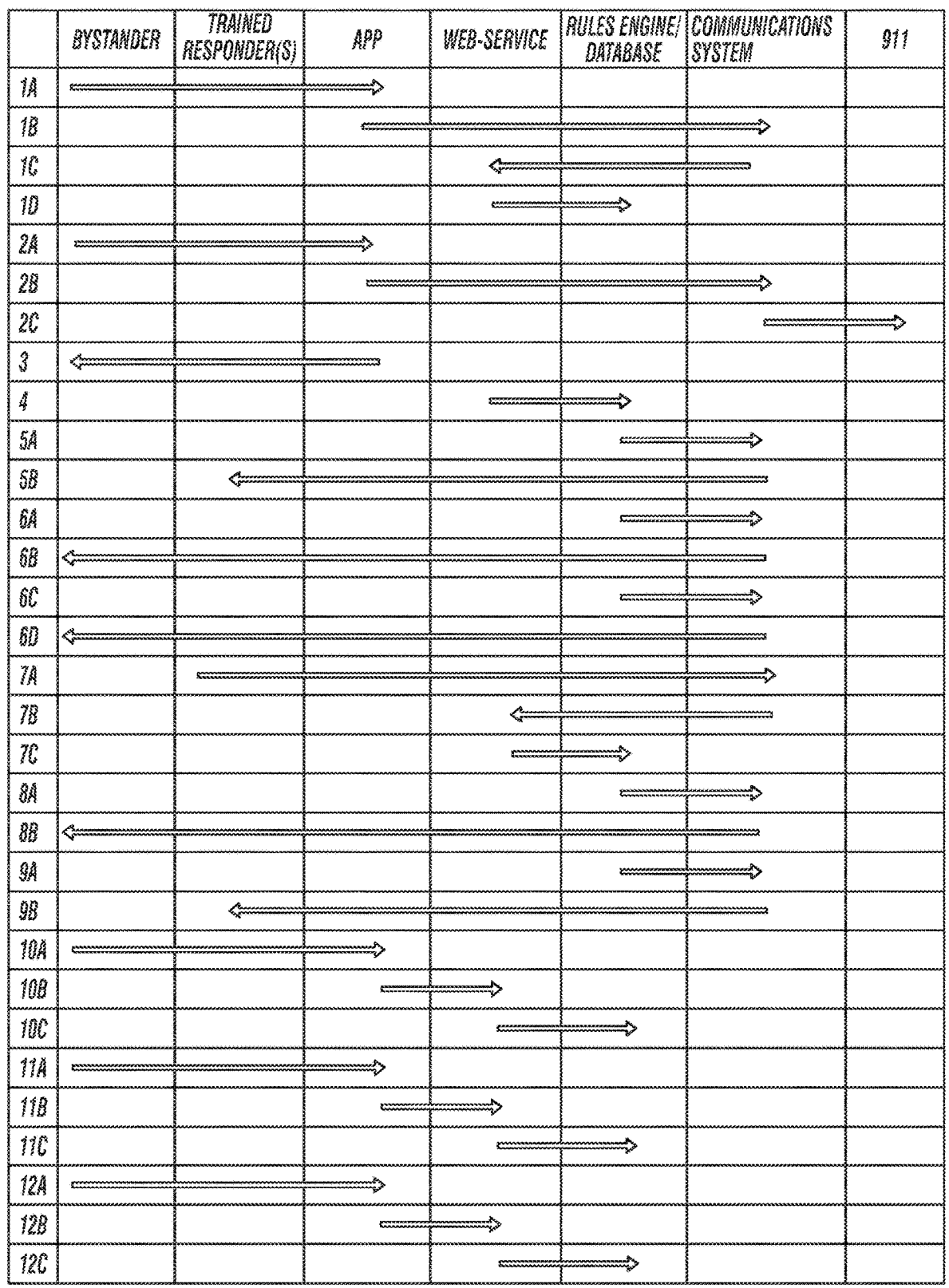
FIG. 6 is a flow diagram showing the sequence of operations during an SCA emergency event according to the invention.

FIG. 6 is a flow diagram showing the sequence of operations during an SCA emergency event according to the invention. The system for such application is architecturally similar to the discussed above for a generic emergency event, for example as discussed in connection with FIGS. 1 and 2. Those skilled in the art will appreciate that some variations, all within their skill, may be made as appropriate to implement this embodiment of the invention.

Database

In addition to that data stored in connection with a generic emergency response system, as described above, data stored in database for this embodiment of the invention also includes the location of AEDs by organization, facility, address, and location in facility, such as floor, and a specific description of location, e.g. 9th floor elevator South; GPS coordinates; date of last successful maintenance; and date of pad and battery expiration.

All communications are logged in the database and there is a report for each incident. Aggregate reports are generated across multiple incidents and include, for example:
1. Date, time, and GPS location of the alert;
2. Who initiated the alert, by cell phone and GPS location;
3. Who is notified of the alert, by cell phone number;
4. Date and time of notification;

5. Who responds to the alert, by cell phone number and GPS location;
6. Date and time that information regarding AED locations is sent to each responder via the communication system;
7. Date and time of notification of responding, using GPS if responder had APP;
8. Date and time of arrival of first trained responder;
9. Date and time that an AED is attached; and
10. Date and time of EMS arrival.

Sequence of Activities/Communications in an SCA Emergency

In FIG. 6:

Step 1. bystander of SCA emergency initiates emergency response notification system via mobile application ("APP"):
- 1A: bystander to APP—bystander of SCA emergency initiates emergency response notification system via APP by accessing and using the App on a phone, tablet, etc.; the bystander communicates to APP, for example by typing or voice input, the specific location within the facility, e.g. 3rd floor bathroom;
- 1B: APP to communication system;
- 1C: Communication system to Web service; and
- 1D: Web service to rules engine/database—Data input by the bystander, e.g. via a cellular service, WIFI, etc. is transmitted via the Web service to the rules engine/database.

Step 2. bystander to 911—bystander of SCA calls 911 directly from the APP:
- 2A: bystander to APP;
- 2B: APP to communication system; and
- 2C: Communication system to 911.

Step 3. App to bystander—bystander of SCA receives optional instructions to initiate resuscitation on the victim via APP.

Step 4. Web service to rules engine/database—The Web service runs a rule-driven query of rules engine/database. This query includes, for example:
a. Comparing location of event to nearest facility having trained responders;
b. Locating nearest trained responders in facility;
c. Prioritizing notification of the trained responders by rules that determine the level and type of training, competence, proximity;
d. Locating nearest AEDs; and
e. Prioritizing by rules that evaluate proximity to the event, and AED functionality.

Step 5. A message containing specific information is sent to selected trained responders:
- 5A: Rules engine/database to communications system— Rules engine/database generates message; and
- 5B Communications system to trained responders—Communications system communicates the following information to selected trained responders: The specific location of event within the facility with instructions to respond prioritized by trained responder training, competency and proximity rules.

Step 6. Messages sent to the bystander informing the bystander how many trained responders have been notified:
- 6A: Rules engine/database to communications system— Rules engine/database generates message; and
- 6B: Communications system to bystander—Communications system sends a message to the bystander.

If no responders are available, a message sent to the bystander informing the bystander of the location of the nearest AEDs, prioritized by functionality rules:
- 6C: Rules engine/database to communications system— Rules engine/database generates message; and
- 6D: Communications system to bystander—Communications system sends the message to bystander.

Step 7. Trained responder responds—Trained responders respond to the alert text with a confirmation message that communicates to the database via the Web service indicating that they are responding. The message generates a geo-location of the trained responder:
- 7A: Trained responder to communication system;
- 7B: Communication system to Web service; and
- 7C: Web service to rules engine/database.

Step 8. Messages sent to the bystander—As each trained responder responds to the alert, indicating whether the bystander is coming or not coming to assist, the bystander receives messages:
- 8A: Rules engine/database to communications system— Rules engine/database generates the message; and
- 8B: Communications system to bystander—Communications system sends the message to bystander.

Step 9. Messages sent to trained responders—After a trained responder responds to the alert indicating that the trained responder is coming to assist, the en route trained responders receive a message containing the location of nearest functional AEDs:
- 9A: Rules engine/database to communications system— Rules engine/database generates message indicating location of nearest functioning AEDs; and
- 9B: Communications system to trained responders— Communications system sends a message indicating the location of the nearest functioning AEDs to the trained responders who are en route.

Step 10. bystander to APP—bystander records time of arrival of first trained responder via the APP, which uses the Web service to record data in the database:
- 10A: bystander to APP;
- 10B: APP to Web service; and
- 10C: Web service to database.

Step 11. bystander to APP—bystander records time that the AED is attached via the APP, which uses the Web service to record data in the database:
- 11A: bystander to APP;
- 11 B: APP to Web service; and
- 11C: Web service to database.

250 Step 12. bystander to APP—bystander records EMS arrival via the APP, which uses the Web service to record data in the database:
- 12A: bystander to APP;
- 12B: APP to Web service; and
- 12C: Web service to database.

Sequence of Activities/Communications in a Non-Medical Emergency (NME)

Figure 7:
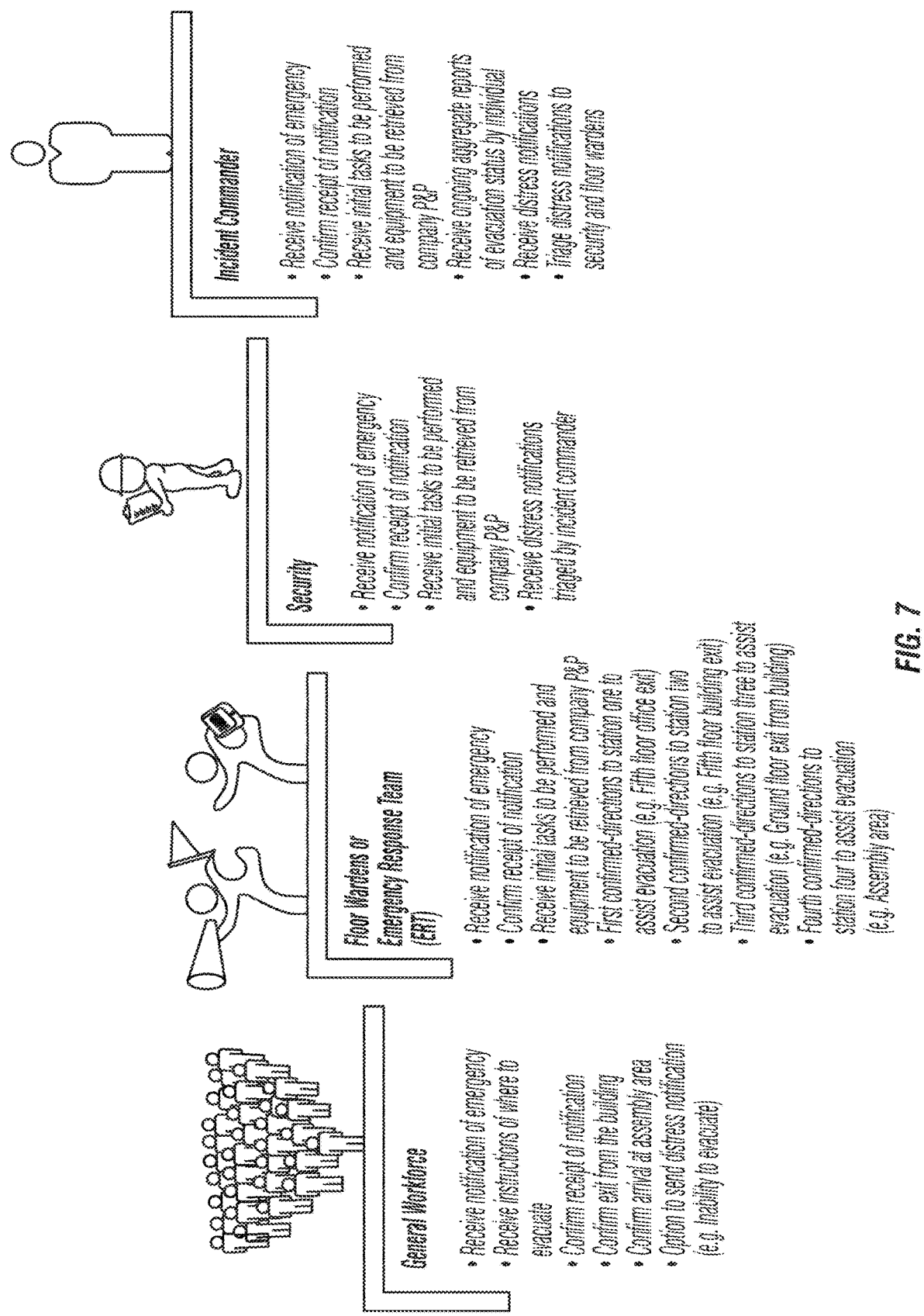
FIG. 7 is a flow diagram showing a non-medical emergency response model according to the invention.

FIG. 7 is a flow diagram showing a non-medical emergency response model according to the invention, in which the relationship between the general workforce, floor wardens and/or emergency response team, security staff, and incident coordinator is shown. This model is discussed in detail below.

Figure 8A:
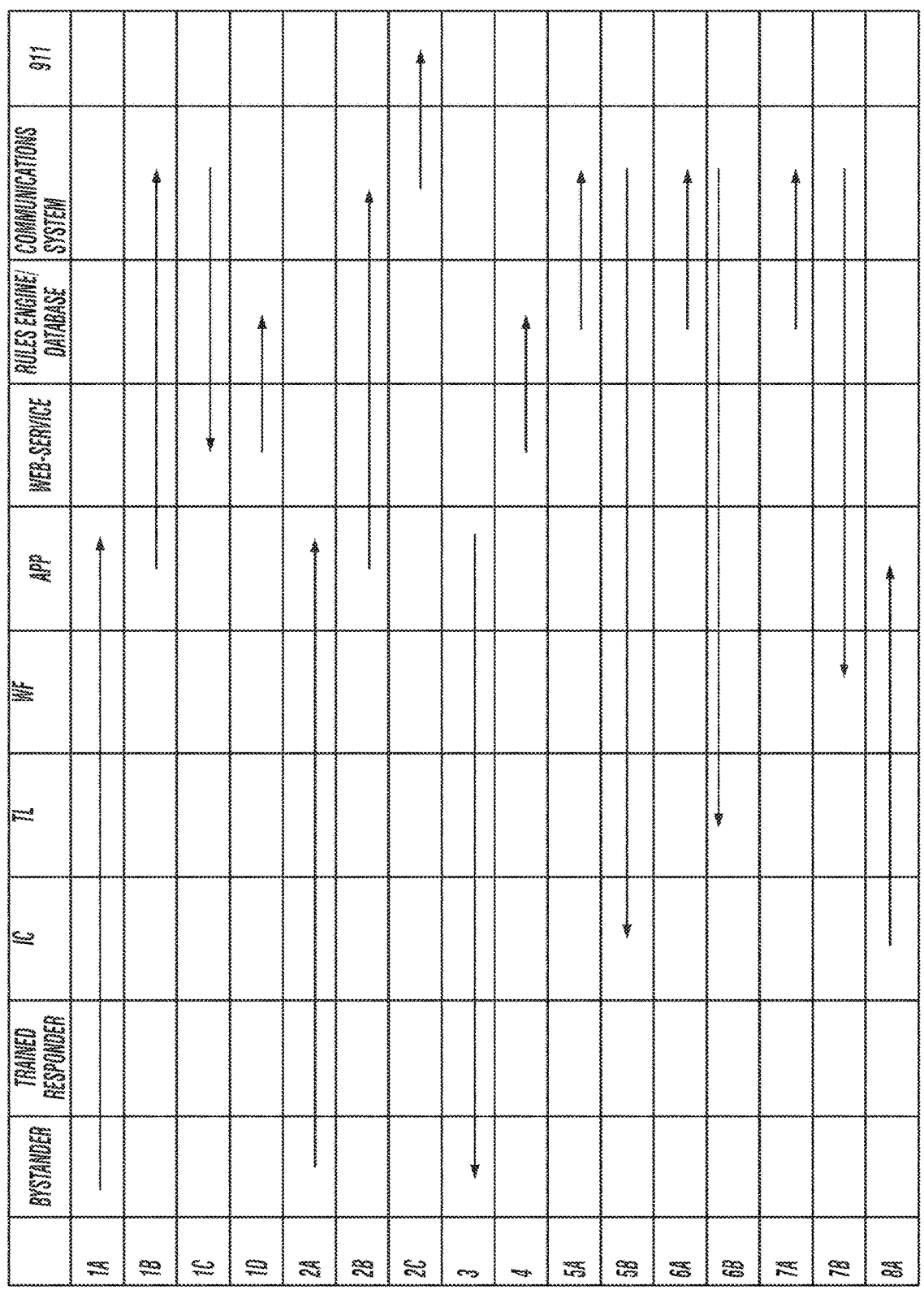
FIGS. 8A-8C are a flow diagrams showing the sequence of operations during a non-medical emergency event according to the invention.
Figure 8B:
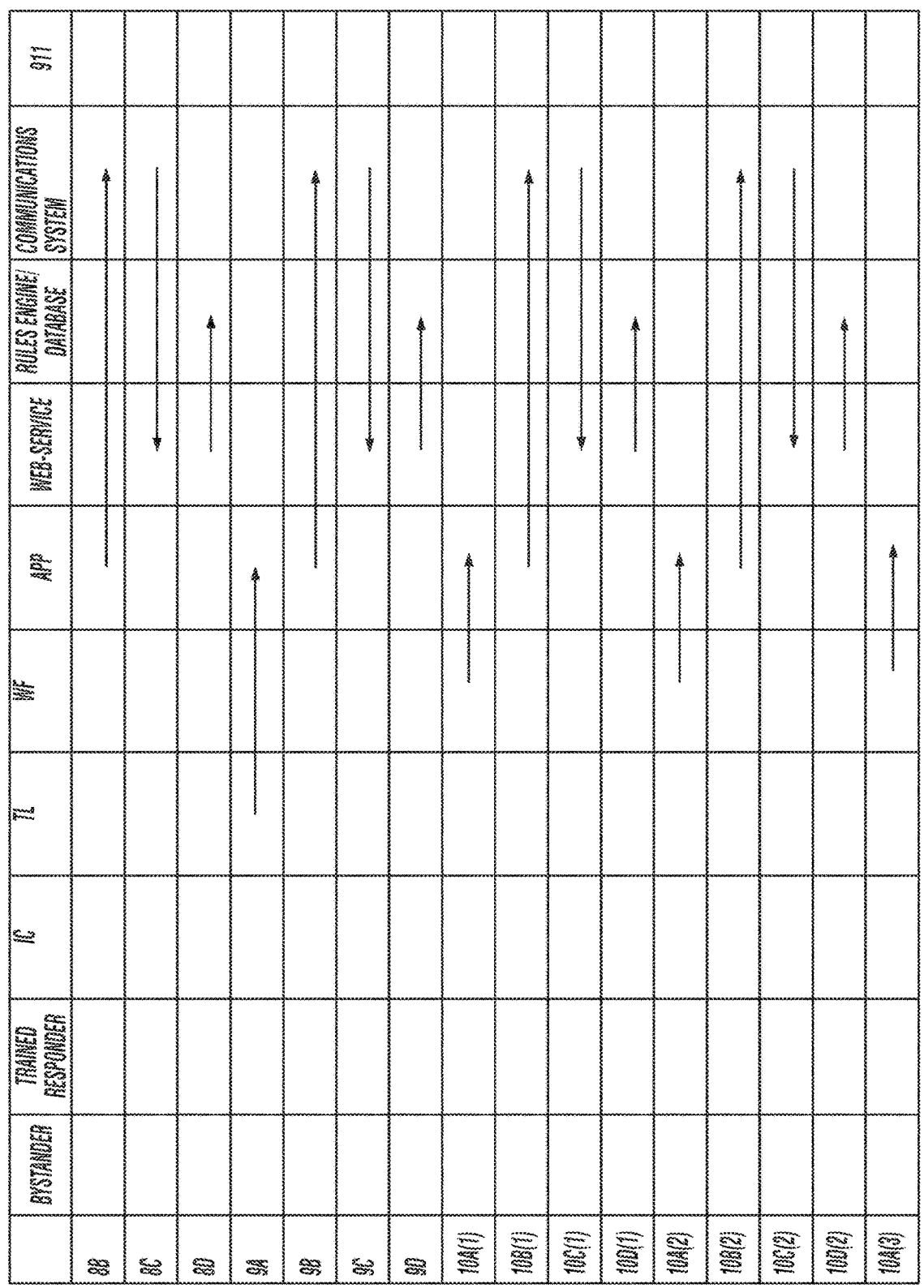
Figure 8C:
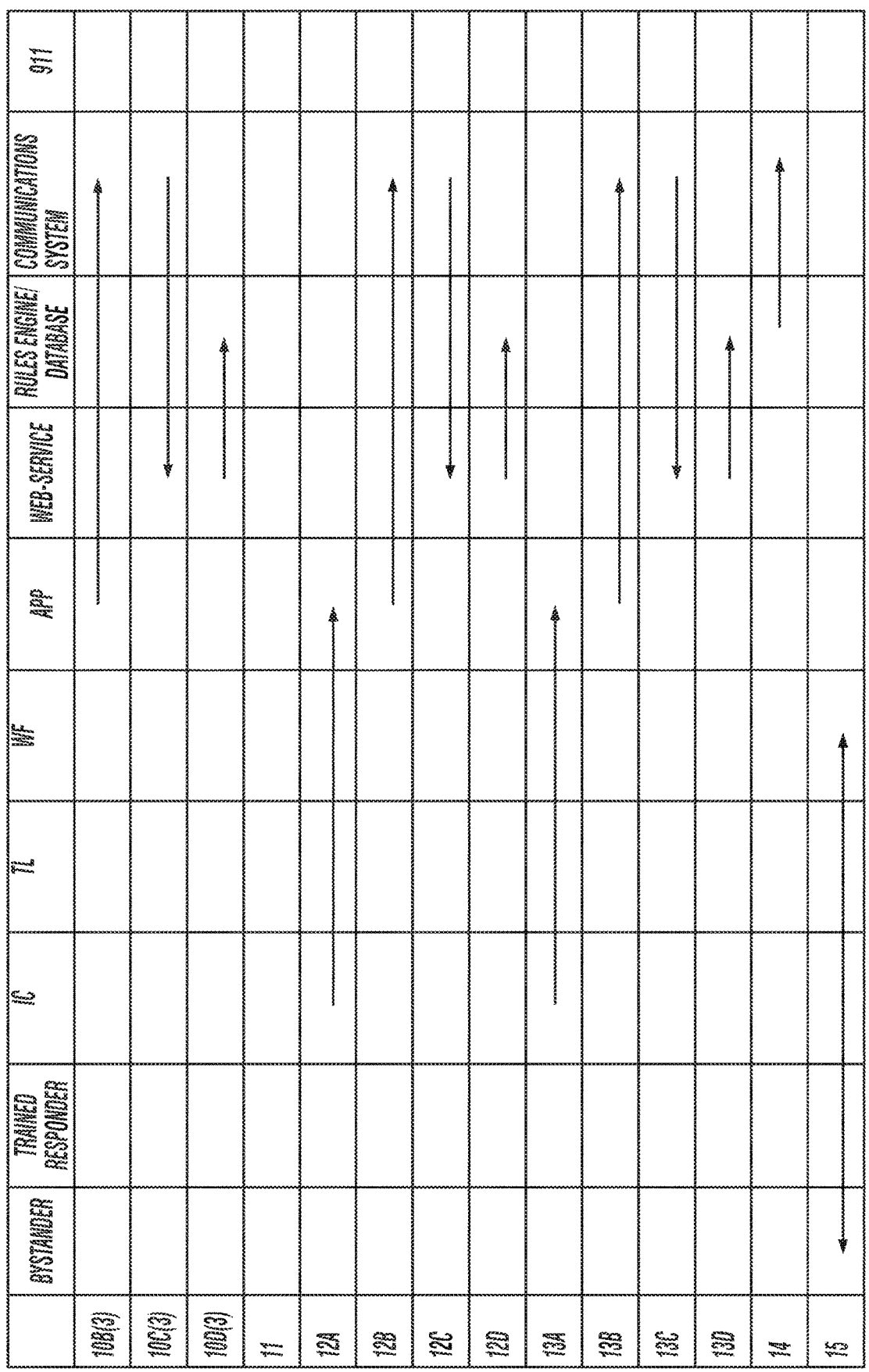

FIGS. 8A-8C are a flow diagrams showing the sequence of operations during a non-medical emergency event according to the invention.

In FIGS. 8A-8C:

Step 1. Bystander of NME initiates emergency response notification system via mobile application (APP):
- 1A: Bystander to APP—bystander of NME emergency initiates emergency response notification system via APP by accessing and using APP on phone, tablet, etc.;

Bystander communicates (type/vocal input) to APP the specific location within the facility, e.g. 3rd floor bathroom;

1 B: APP to communication system;

1C: Communication system to Web-service;

1 D: Web-service to rules engine/database—Data inputted by bystander via cellular service, WIFI, and/or other is transmitted via the Web-service to the rules engine/database:

a. Secondary screen allows selection between medical and non-medical emergencies; or b. Secondary screen uses drop down screen to select type of medical or non-medical emergency; and/or c. Permits text description of emergency.

Step 2. Bystander to 911—Bystander of NME calls 911 directly from APP:

2A: Bystander to APP;

2B: APP to communication system; and

2C: Communication system to 911.

Step 3. App to Bystander—Bystander of NME receives optional instruction to assist in emergency based on type of emergency and competence level, i.e. nearest fire extinguisher with instructions on how to use it if there is a small fire.

Step 4. Web-service to Rules Engine/Database—Web-service runs a rule-driven query of the rules engine/database. This query includes:

Comparing location of event;

Identifying IC, TL, and/or WF for facility;

Selecting communications and content based on defined roles, i.e. IC, TL, WF;

Identifying nearest facility with trained responders;

Prioritizing notification of personnel by roles;

Locating nearest required equipment based on designated roles, type of emergency, and availability of equipment by designated geographic area; locating nearest AEDs/medical equipment;

Prioritizing by rules that evaluate proximity to event and AED/medical; and

Prioritizing by rules that evaluate type of emergency, proximity to event, and equipment functionality.

Step 5. Message containing specific information sent to IC:

5A: Rules Engine/Database to Communications System—Rules Engine/database to communications system generates message; and 5B: Communications System to IC—Communications system to IC communicates the following information: notification of emergency, location, and type of emergency with instructions for completing initial pre-configured series of actions and to confirm receipt of notification.

Step 6. Message containing specific information sent to TL:

6A: Rules Engine/Database to Communications System—Rules engine/database to communications system generates message; and 6B: Communications System to TL—Communications system to TL communicates the following information: notification of emergency, location, and type of emergency with instructions for completing initial pre-configured series of actions and to confirm receipt of notification, including to retrieve equipment, supplies, assume proper location, assist with evacuation, and confirm receipt of notification. In addition, report initial and ongoing problems to IC. Variable content for initial instructions includes ongoing communications, e.g. Doug is unable to evacuate, because he is trapped under bookshelf that fell; Mary needs a disability stair chair to exit; there is a secondary fire in the hallway near the 3rd floor bathroom; etc.

Step 7. Message containing specific information sent to WF:

7A: Rules Engine/Database to Communications System—Rules engine/database to communications system generates message; and 7B: Communications System to WF—Communications system to WF communicates the need to initiate evacuation procedures including location and/or directions to nearest evacuation exit from their location, and assembly point address, and to confirm receipt of notification. This can include variable quantity and quality of content; and use of variable technologies to assist with locating exits, such as Bluetooth or wireless transmitter technology to assist WF to reach evacuation exit rapidly. The message includes instructions to respond to alert text with notification that they have evacuated and reached assembly point.

Step 8. IC to APP to Communication System to Web-Service to Rules Engine/Database, where IC responds to the alert text, with communication to database via the Web-service indicating that they are assuming command, and if IC does not respond, an alternate pre-designated authority is notified:

8A: IC to APP—IC responds to the alert text, with communication to database via web-service indicating that they are assuming command;

8B: APP to Communication System;

8C: Communication System to Web-Service; and

8D: Web-Service to Rules Engine/Database—Data inputted by IC via cellular service, WIFI, and/or other is transmitted via the Web-service to the rules engine/database.

Step 9. TL to APP to Communication System to Web-Service to Rules Engine/Database. TLs respond to the alert text with communication to database via the Web-service, indicating that they are responding and assuming their responsibilities. If no response, the IC assesses the need for additional personnel notification:

9A: TL to APP—TLs respond to the alert text with communication to database via the Web-service, indicating that they are responding and assuming their responsibilities;

9B: APP to Communication System;

9C: Communication System to Web-Service; and

9D: Web-Service to Rules Engine/Database—Data inputted by IC via cellular service, WIFI, and/or other) is transmitted via the Web-service to the rules engine/database.

Step 10. WF to APP to Communication System to Web-Service to Rules Engine/Database. WF responds to the alert text with communication to the database via Web-service, indicating that they have received notification:

10A(1): WF to APP—WF responds to the alert text with communication to database via the Web-service, indicating that they have received notification;

10B(1): APP to Communication System;

10C(1): Communication System to Web-Service; and

10D(1): Web-Service to Rules Engine/Database—Data inputted by IC via cellular service, WIFI, and/or other is transmitted via the Web-service to the rules engine/database. WF clicks notification on evacuation screen that they have successfully evacuated.

10A(2): WF to APP—WF clicks notification on evacuation screen that they have successfully evacuated;

10B(2): APP to Communication System;

10C(2): Communication System to Web-Service; and

10D(2): Web-Service to Rules Engine/Database—Data inputted by IC via cellular service, WIFI, and/or other is transmitted via the Web-service to the rules engine/database. WF clicks notification on assembly screen that they have successfully arrived at assembly point.

10A(3): WF to APP—WF clicks notification on assembly screen that they have successfully arrived at assembly point;

10B(3): APP to Communication System;

10C(3): Communication System to Web-Service; and

10D(3): Web-Service to Rules Engine/Database—Data inputted by IC via cellular service, WIFI, and/or other is transmitted via the Web-service to the rules engine/database.

Step 11. RE to IC: Database/rules engine generates communication to IC providing continuously updated and/or compiled report of personnel who have successfully evacuated and reached assembly point, including a continuously updated report of all personnel who have confirmed receipt of notified of emergency and their GPS location, a continuously updated report of all personnel who have provided notification of evacuation and their GPS location, and a continuously updated report of all personnel who have provided notification of arriving at the assembly area and their GPS location.

Step 12. IC to APP to Communication System to Web Service to Rules Engine/Database: IC indicating time of arrival of each EMS/Fire/Police arrival.

Step 13. IC to APP to Communication System to Web Service to Rules Engine/Database: IC requests APP geo-locate location of all personnel.

Step 14. Database/Rules engine to Communication System: Dynamically generated map of cellphones locating personnel who have not evacuated as per GPS coordinates within the facility and require assistance.

Step 15. Ongoing communication between ICs, TLs, and WF:

Ongoing communication between ICs, TLs, and WF including requests for assistance; identification of injuries, e.g. Joe broke leg from falling debris, Doug had a heart attack, Sam sustains major bleed from falling glass; identification of secondary emergencies, e.g. fire following earthquake, do something on the chart that indicates all the way across the IC, WF, TL, and people ongoing communications.

Workforce Evacuation Notification

FIGS. 9A-9D area series of screenshots showing a workforce evacuation notification sequence according to the invention, which an individual uses the APP to send a notification that they have received the evacuation notification (FIG. 9A), that they have exited the building (FIG. 9B), and that they have arrived at their pre-designated assembly point (FIG. 9C); or that they are in distress (FIG. 9D).

Embodiments of the invention identify evacuation exits with a transmitted signal to direct workforce members to a nearest evacuation exit. The signal can comprise any one or more of a Wi-Fi-based IP addresses, Bluetooth, radio, satellite, pre-placed transmission equipment proximate to said exits, Wi-Fi-based signals transmitted from exit doors at said exits. Wi-Fi signals from a nearest router.

Embodiments of the invention locate non-evacuating personnel with a transmitted signal. The signal can comprise any one or more of Wi-Fi-based IP addresses, Bluetooth, radio, satellite, pre-placed transmission equipment proximate to said exits, Wi-Fi-based signals transmitted from exit doors at said exits, Wi-Fi signals from a nearest router. In embodiments of the invention, the signal includes instructions in any of text and graphic format to said non-evacuating personnel directing them to a nearest exit. Notifications can include any one or more of text, graphics, voice, and visual dynamic directions, such as GPS directions (WAZE).

In embodiments of the invention, location information can be determined from, for example, the elevation component of GPS, where the height of each floor is pre-calculated to locate the individual by floor. Location information can also be determined from the APP using the proximity of the phone signal to the IP of the routers in the facility; using the proximity of the phone signal to the wireless signal of a transmitter located in the evacuation door; using the proximity of the phone signal to the Bluetooth signal of a transmitter located on the evacuation door; or with any device that can transmit and receive signals. Embodiments of the invention use any of the foregoing techniques to create a dynamic map of the location of workforce personnel, trained responders, emergency equipment, exit doors, etc.

Role-Based Task Generation

Figure 10:
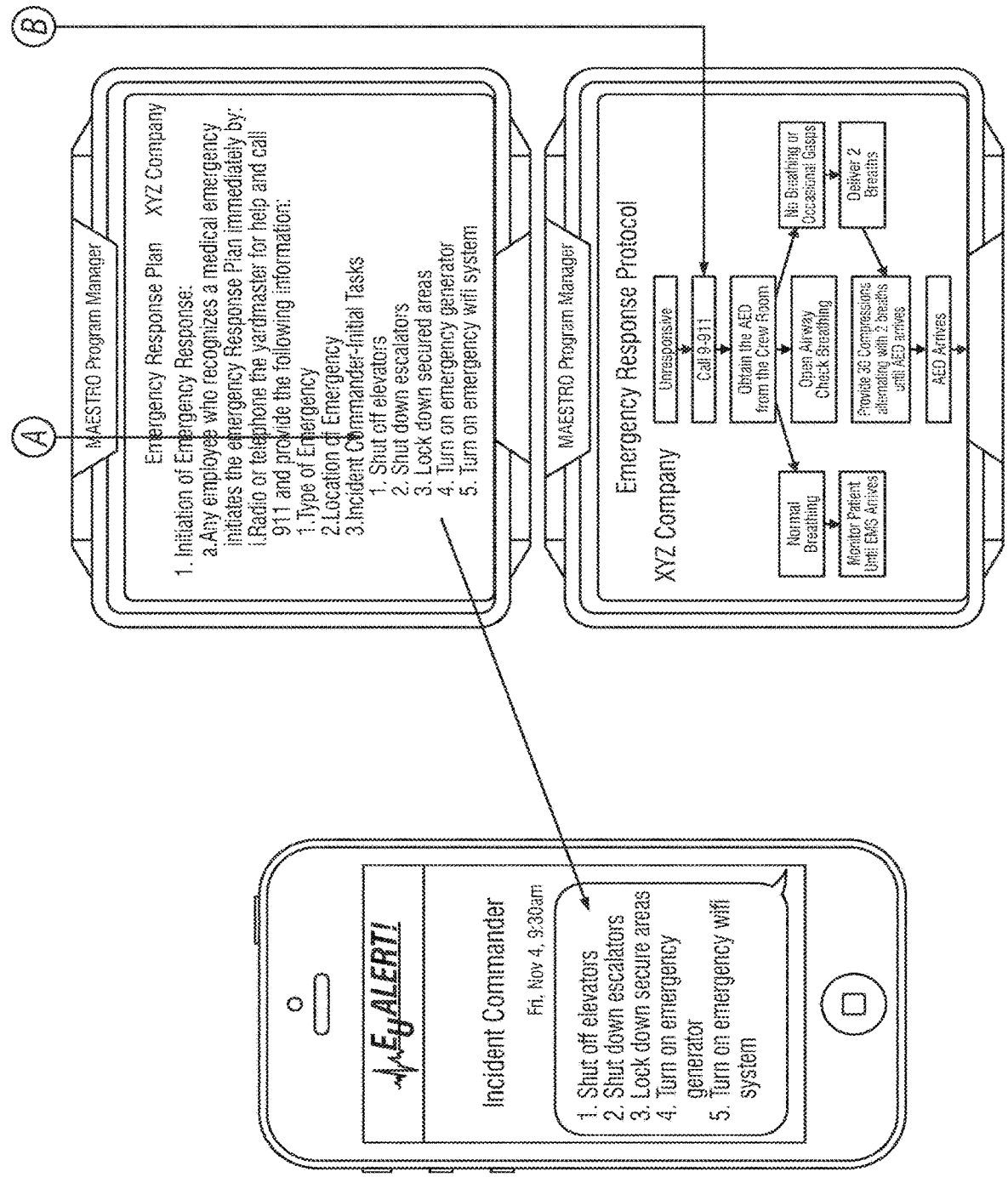
FIG. 10 is a flow diagram showing an example of how the role-based details are lifted out of the emergency response protocol and transmitted to the appropriate role-based individual in an emergency, where an electronic site survey generates organization specific emergency response protocols that detail role-based tasks according to the invention.

FIG. 10 is a flow diagram showing an example of how the role-based details are lifted out of the emergency response protocol and transmitted to the appropriate role-based individual in an emergency, where an electronic site survey generates organization specific emergency response protocols that detail role-based tasks according to the invention.

In FIG. 10, the top screen is a sample frame of an electronic site survey that is completed by an organization. Authorized personnel complete text screens in answer to questions that reflect the customized information that is included in their emergency response policies, procedures, plans, and protocols. For example, in #51, the organization states that the phone number that must be dialed to reach an outside line and call 911 is actually 9-911. This phone number is incorporated into their Emergency Response Protocol (bottom screen on the right in FIG. 10). This field is transmitted to the mobile application to individuals who are attempting to initiate a call to 911 from a company landline.

In example #53, the initial tasks of the Incident Commander are determined and typed into the electronic site survey (top of FIG. 10) by the incident commander or his designee who is authorized to develop the organization's policies and procedures. Once it is confirmed that these are the organizational IC's initial responsibilities in an emergency, they are incorporated into the organization's emergency response plan (top frame in lower half of page on the right In FIG. 10). At the time of an emergency, these tasks are transmitted to the IC on his mobile application, upon confirmation of receipt of notification of an emergency from a bystander and/or witness for an emergency that requires initiation of a command structure.

Alert Cancellation

Figure 11:
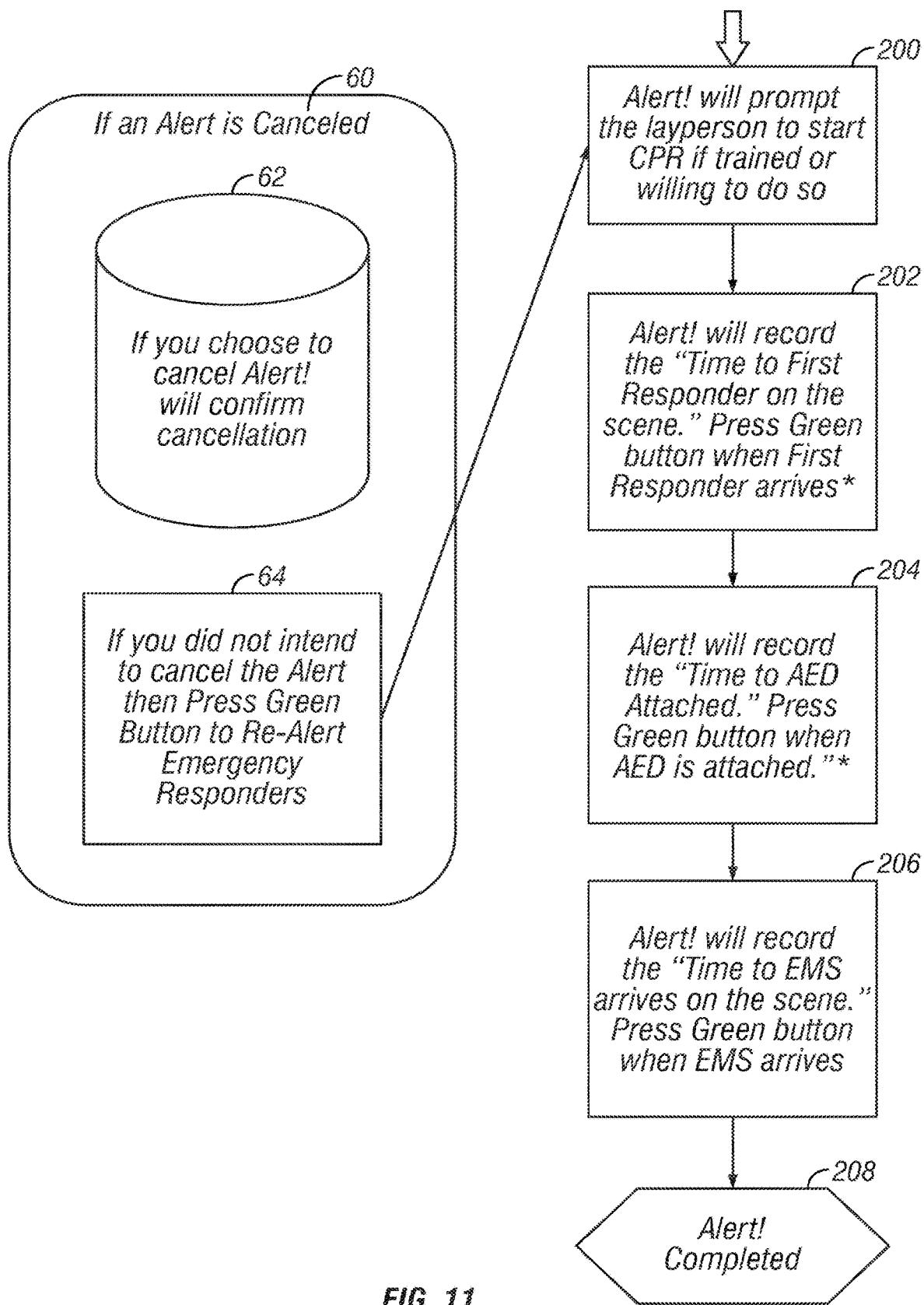
FIG. 11 is a flow diagram showing the cancellation of an alert according to the invention.

FIG. 11 is a flow diagram showing the cancellation of an alert according to the invention. In FIG. 11 if an alert is to be cancelled 60, the APP provides a message the bystander 62 advising the bystander that the alert can be cancelled. A button 64 can then be selected by the bystander to cancel the alert.

If the bystander did not intend to cancel the alert, the cancellation can be rescinded by pressing a button, e.g. press green to re-alert the emergency responders. The alert is then reinstituted. For example, during an alert the system alerts the bystander to take an action (2), such as applying CPR if trained or willing to do so. The systems records that time at which the first responder is on the scene (2). The APP provides a button for the bystander to press indicating the arrival of the first responder. The system also records such activities as the attaching of an AED to the victim (2). Again, a button can be pressed by the bystander to indicate this action has taken place. The system also records when an EMS arrives (2). Again, a button can be pressed by the bystander to indicate this event has taken place. Thereafter, the alert is completed (2).

The APP

The APP is a mobile application that alerts all trained first responders to the scene of an emergency, such as a sudden cardiac arrest (SCA) or medical emergency. Users may be certified trained responders or laypersons. For example, consider the following participants in a sudden cardiac arrest (SCA) or medical emergency:

1. The victim of the medical emergency;
2. Bystanders to the event, whether laypersons or trained responders; and
3. Certified first responders who are not at the event.

Embodiments of the Invention Include:

Real Life Event

As part of an organization's emergency response plan, the general workforce downloads and initially registers the mobile application. Bystanders to the event activate the APP and verify the event location. If the event occurs at the location for which the bystander originally registered, then the bystander types in the specific location of the event into provided field. If the bystander is at a different location, then a drop-down menu is provided for an alternative facility where the bystander is now located. (In embodiments of the invention, GPS is used as first determinant of location and, if it is not available, then the system falls back on a pre-configured location, and the user must change location by a drop-down menu.

The APP communicates the location of the emergency to the database and rules engine system via a Web service. The rules engine uses an algorithm and searches the specified company and facility for a prioritized call-to-action list of certified first responders. In embodiments of the invention, the order of priority of called responders is the most recently trained responders, certified responders, certified trainees, and trainees requiring re-certification. The Web service compiles a list of the certified first responders in order of most recent skills dates, i.e. certification dates, to least recent skills dates.

The system sends both an email and a text message to these certified first responders at the facility. To send the email or a text message, the APP sends a request to the Web service. The Web service sends out the emails through, for example, SMTP. The SMS gateway captures the original call-to-action ID and establishes communication between the bystander and the facility alerted responders. Each responder receives multiple alerts via SMS and emails to ensure that this notification is unique from typical SMS/email reception. Upon receiving an alert, the responder replies via SMS/email if they are on the way. The bystander receives a notification on their smartphone, tablet, etc. of the number of responders that have been alerted and the number of responders that are on the way. The APP performs tracking of the event's vital clinical performance milestones, such as time to first responder arrival; time to AED Pad attachment; and time to EMS arrival.

Facility Wide Drill

This function allows trained responders to practice their facility's emergency response plan and has the same functionality as a real-life event, except that the actual content of the email and text alerts indicates "THIS IS A DRILL." Text messages and email are only sent one time.

Drill Code Option

This embodiment of the invention provides the same functionality as the facility wide drill, except this embodiment is class specific and is used during a training class. This means that the APP is activated, and messages are sent to a specific subset of people. Rather than the algorithm pulling certification dates and sorting responders to receive alerts, the participants all enter a specific drill code. Those entering the drill code receive the email and text. The email and text are sent as many times as the APP button is pushed. This drill code can be used regardless of company or facility. Thus, trainees from different sites can train together and get alerts.

Operation

Critical to the viability of the APP is the availability of the database and rules engine system that stores the physical facilities and the certified responders who are located at each facility. Responders must complete regular training and drills which are tracked in the database and rules engine system.

Responders receive certifications in areas such as CPR, First Aid, and AED response. Response planning is structured to ensure adequate response time from one or more trained responders within the physical location.

As part of a program rollout at a facility, employees of an organization are encouraged to download and install the mobile APP on their phones. Registration and downloading the App requires that the user enter, for example, a code specific to a certain company. Based on this code, a menu of locations is provided, allowing the user to select the appropriate facility. The list of locations is retrieved from a central Web service over the public Internet. The Web service uses the database and rules engine system to retrieve the list of facilities using the company code.

Once the location is selected, the user also provides his name, email address, and phone number to register the APP. The registration information is passed to the database and rules engine system via another Web service. The information is also stored on the user's phone or tablet. More information about the responders and other members of the emergency response team is stored in the database, but it is not necessarily related to registration for the APP. For example, such information is retrieved based on the individual's role as defined in the database. In fact, in embodiments of the invention responders do not need to have the APP to be contacted. They are automatically contacted once an alert is sent to the database, based on the rules engine determining who is required for the emergency, which is pre-configured by role in the database. Responders are identified in the database, for example, by their email address, cell phone number, name, company, and facility. All of the above information is stored based on identifying the individual in this way, i.e. their training status, their role, and, therefore, the information that they are to receive.

Although responders do not have to be registered to be notified in case of an emergency, they must be registered to send an alert themselves.

In embodiments of the invention, users of the APP are either any of untrained general workforce members who serve as the witness or bystander of the emergency and initiated the notification process and/or initiate the emergency response plan, and trained responders who may also witness an emergency.

Subsequent launching of the APP bypasses the registration process and the user is immediately prompted, "Do you have an Emergency?", to which the user can answer "Yes," "No," or "Drill." If the user answers "Yes," a screen with a large button is presented, that initiates the medical response protocol. Prior to pressing the button, the user can verify their location or enter specific location information, e.g. via touch or dictation. Answering "No" allows users to obtain non-emergency information or change their registration information. Answering "Drill" is discussed below.

When the button is pressed, the notification process begins. The APP invokes another network Web service, including the location, phone number, and name of the initiator. The Web service logs an incident in the database and rules engine system and then retrieves a list of potential responders using the certification data for the facility. The responder list is sorted so that most recently certified responders are at the top of the list and added to a messaging system queue. The service then returns the number of notifications that are queued, and the initiator is told how many messages were sent.

The messaging system sends medical alert text messages to responder phones and also sends email messages as a back-up. The responders do not need an APP to receive these messages. The messaging system interacts with a third-party SMS gateway using its public API to transmit the actual messages. The gateway is configured with a pool of phone numbers and the messaging system transmits the text messages by rotating through the phone numbers pool. This allows transmission of hundreds of emergency notifications within seconds, without drops from phone system carriers, seconds that are critical for a cardiac event. The text message notification includes a prompt to "reply Yes if you will respond" and the SMS gateway is configured to invoke a Web service when it receives such a response. This Web service tracks the responses and sends additional text messages back to the initiator, letting the initiator know that a responder is en route.

After initiating the event notification, the mobile APP user is taken to progressive screens where further progress is tracked. The user is prompted to call the 911 service, then asked to push buttons progressively, e.g. when the responder arrives, when a defibrillator (AED) is attached, and when EMS arrives. Each of these actions interacts with the Web services to record these events along with associated timestamps in the database and rules engine system. Over time, this allows data about such events to be collected, which can be analyzed and summarized to produce response rate studies. The user may also cancel an incident if the notification system was initiated in error. As with the initial notification, a Web service is invoked which determines the list of responders and, in the same manner as before, cancellation messages are sent to the responders.

It is important to practice emergency response events regularly using drills. After registration has been completed, the user also has the option to select "Drill" when launching the mobile APP. As discussed above, there are two types of drills, a facility-wide drill and a classroom drill using a drill code. After pressing "Drill" the user is prompted to enter a drill code for a classroom drill or leave it blank for a facility-wide drill. The facility wide drill is identical to the actual incident notification process described above, except that the notifications clearly include "THIS IS A DRILL" in the text.

The classroom drill requires the instructor or drill coordinator to provide a drill code to all of the participants. The mobile APP users can then enter the drill code and join the drill either as an event initiator or responder. The APP transmits the phone numbers to a Web service which tracks drill codes and participants in the database and rules engine system. Initiators are then taken to through the same screens described above, with the button to begin the notifications. However, the drill code is included in the incident notification Web service and, instead of retrieving all responders at a particular facility, it retrieves only those responders associated with the drill code. In this mode, only the drill code is used for selecting responders.

The drill responders can be selected from across multiple facilities. Drill codes have a limited validity period, e.g. 30 minutes, depending on the class timeframe. Responders are not notified if they joined the drill during a period that has lapsed.

User Interface

FIG. 12-17 are screen shots showing various user screens provided by the APP during an emergency.

Figure 12:
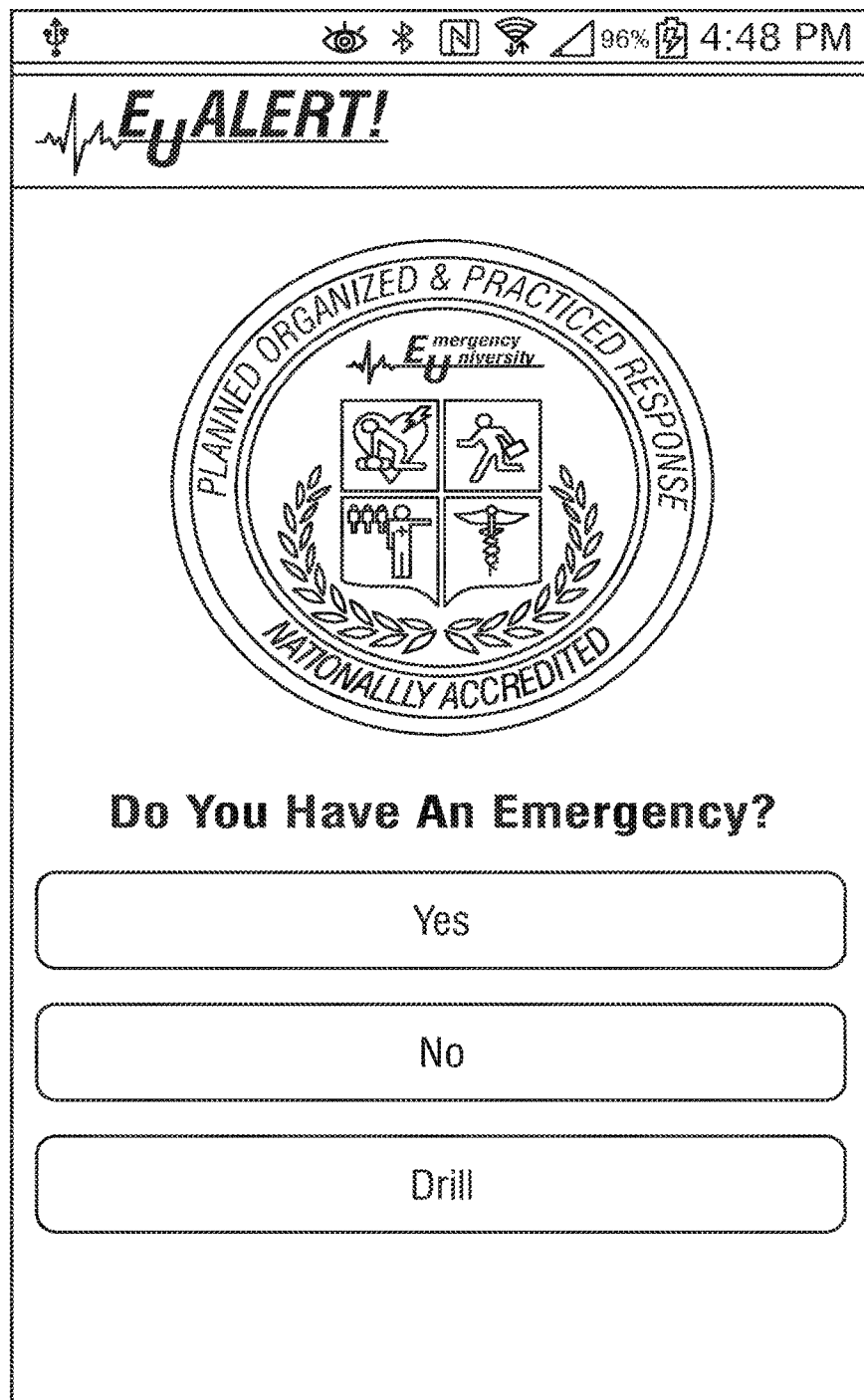
FIGS. 12-17 are screen shots showing various user screens provided by the APP during an emergency.
Figure 13:
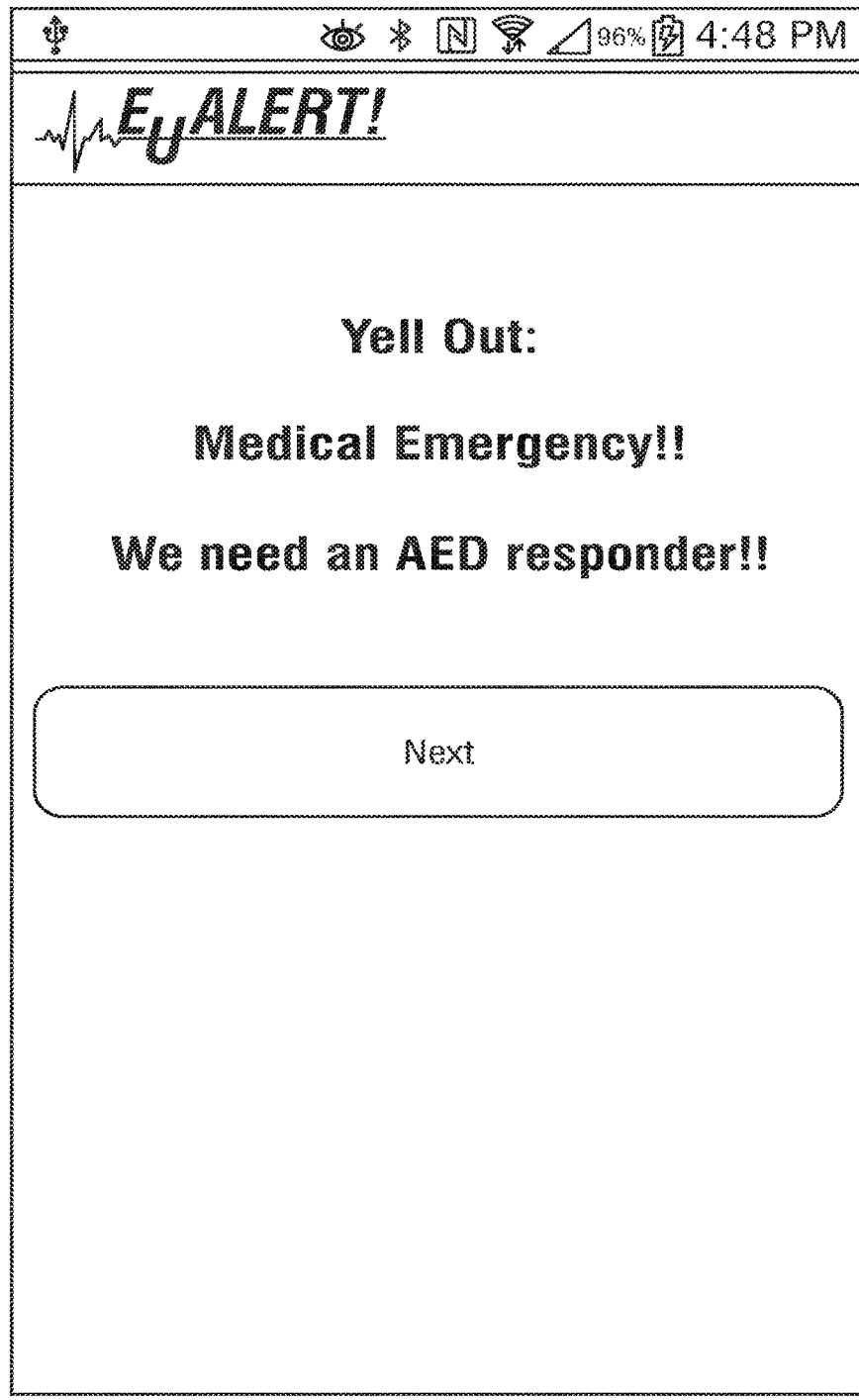
Figure 14:
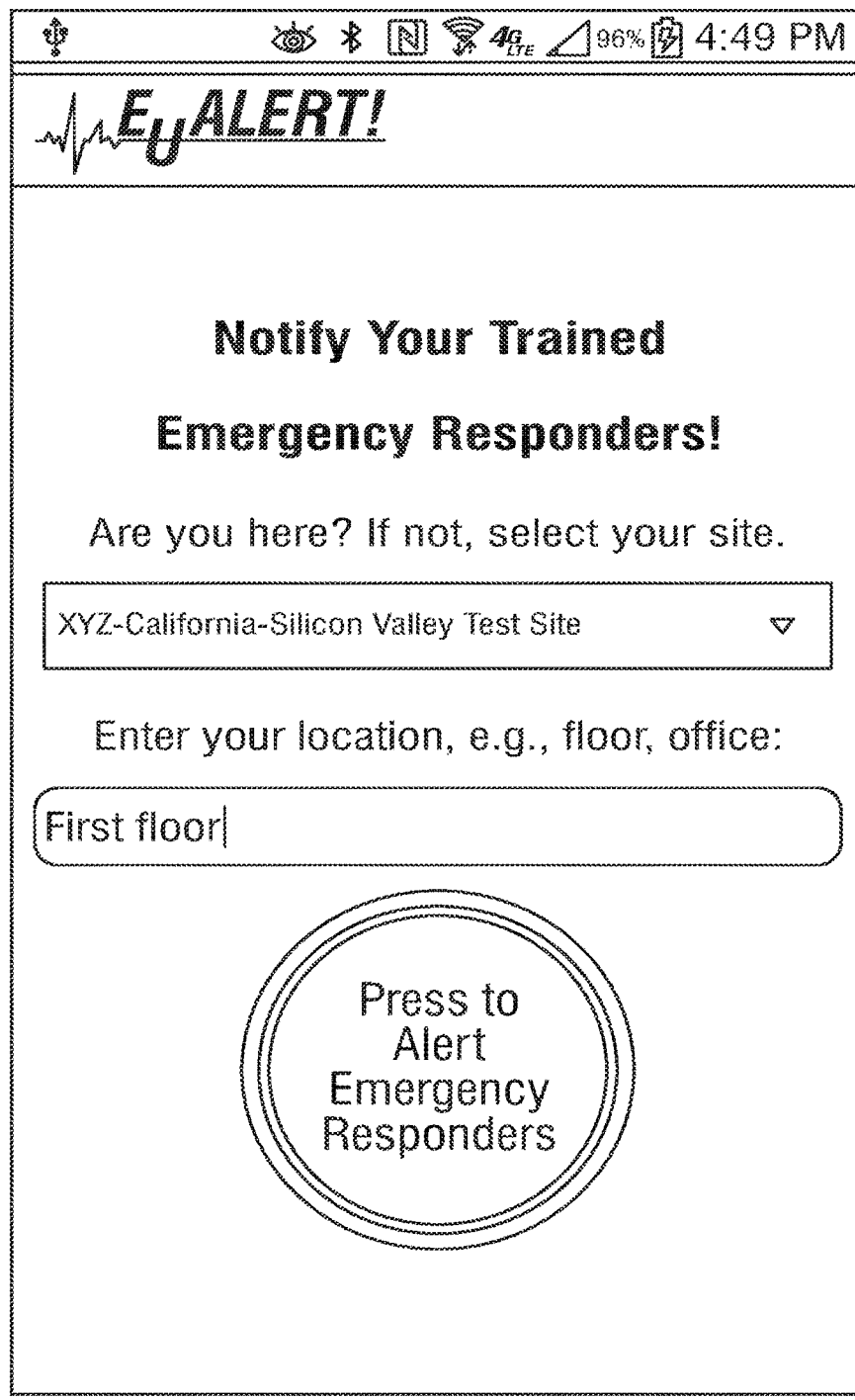
Figure 15:
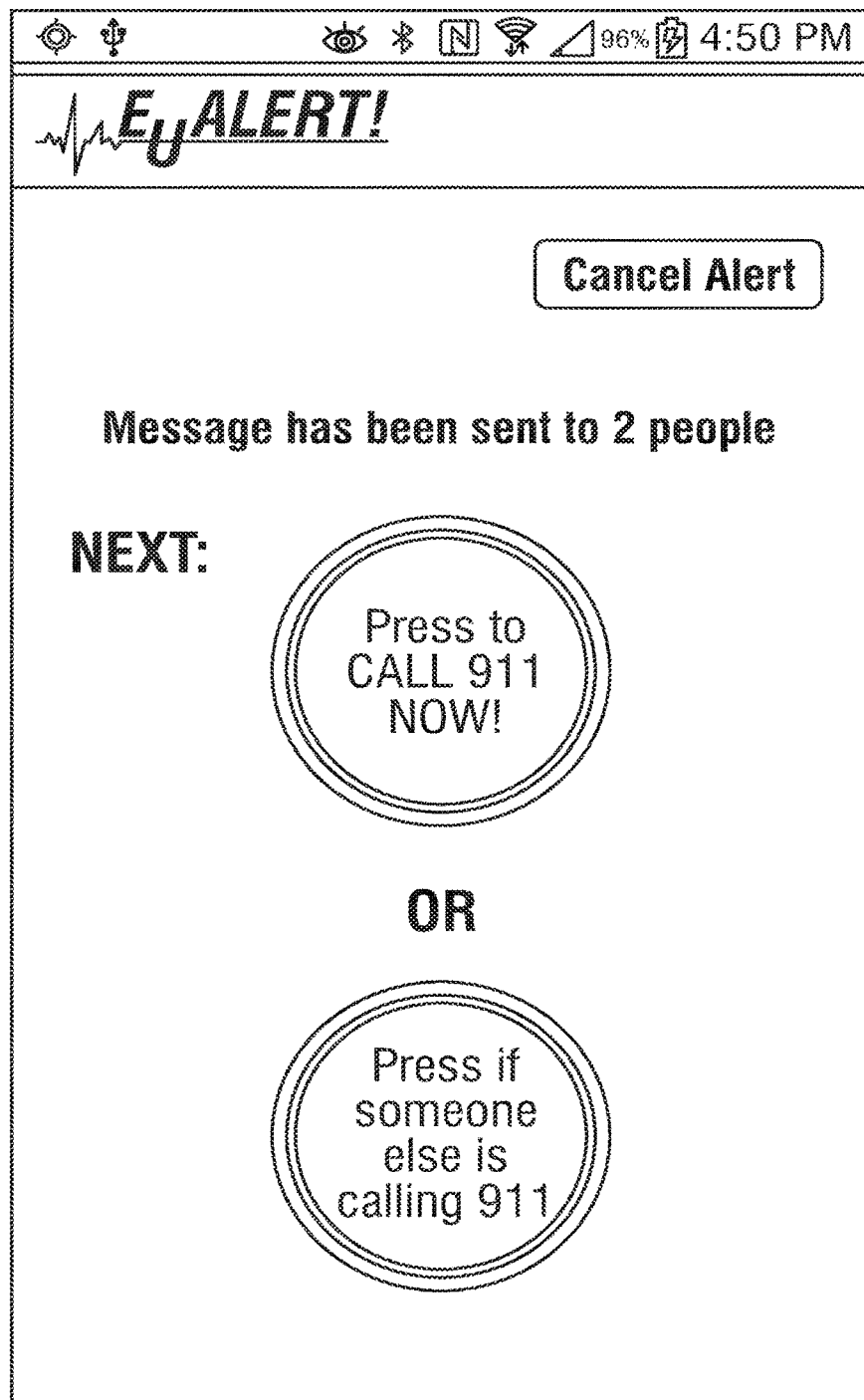
Figure 16:
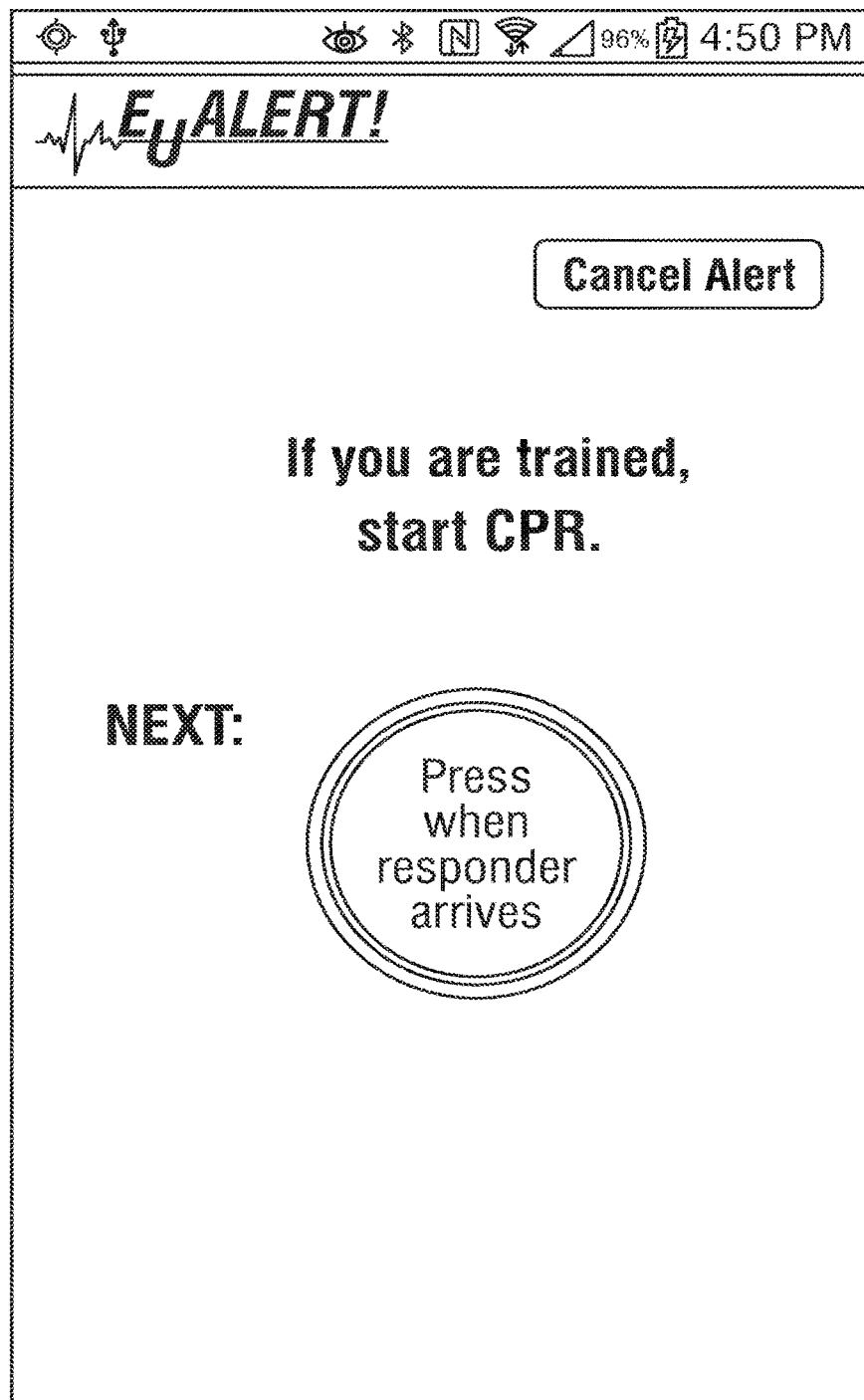
Figure 17:
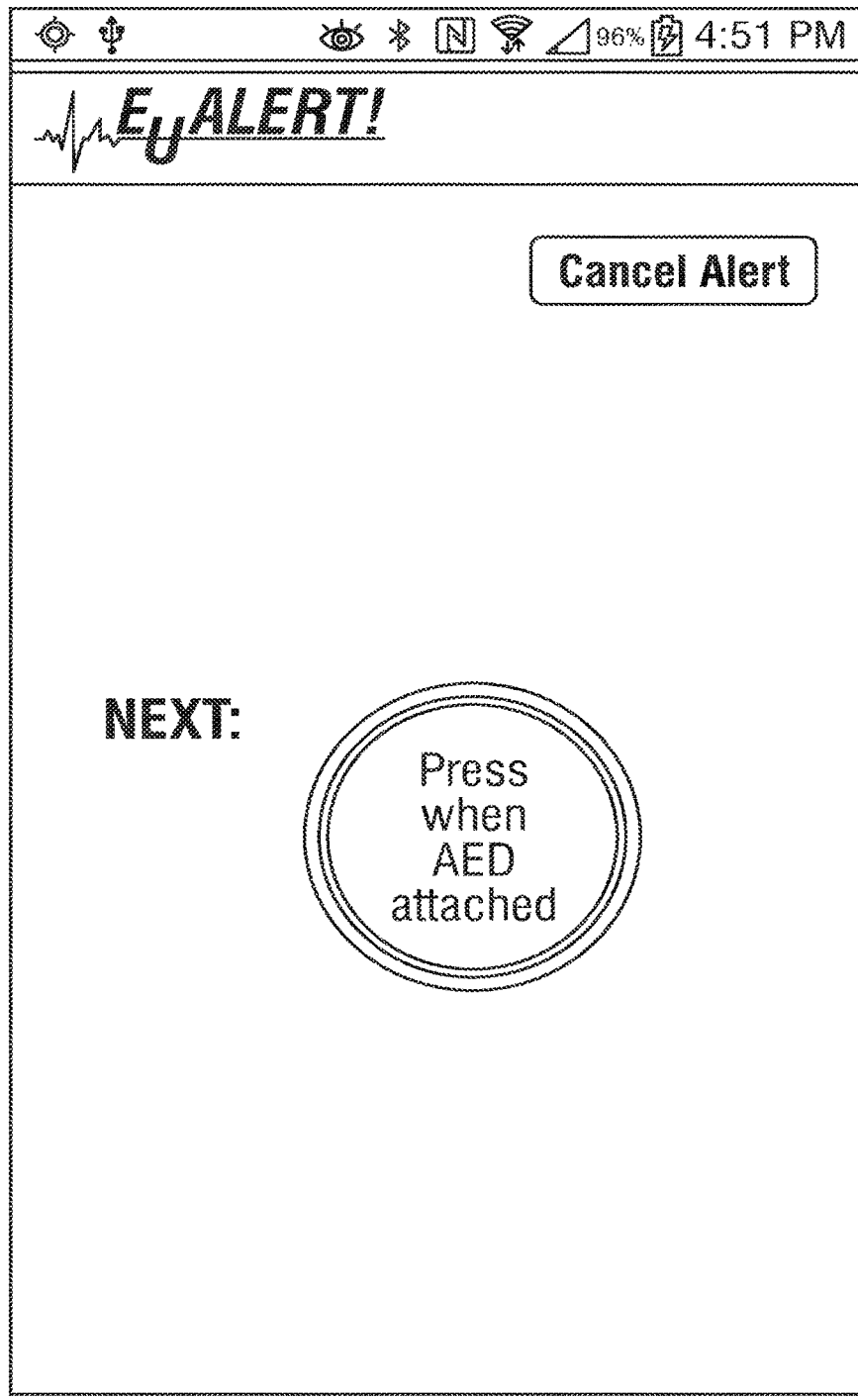

Do you have an emergency? See FIG. 12.

This screen asks the user if they have an emergency and presents them with two options, yes or no. By clicking on the "yes" button the user starts the emergency response sequence. If the user chooses the "no" option they are taken to a menu that provides three choices to learn more about the APP, the AED program, or CPR/AED training.

EU-Alert Information Menu

By clicking on the "no" option in the "do you have an emergency screen" the user taken to this screen which has three informative options which are identical to the "thank you for registering screen."

Emergency Alert Initiated. See FIG. 13.

Initiate the emergency response plan by yelling out Medical Emergency!! We need a responder!! To proceed to the next step, press the "next button."

Notify Your Trained Emergency Responders. See FIG. 14.

Ensure that correct site is highlighted in the drop-down menu. Provide a specific location in the second data field and press the green button to send out the alert to nearby responders.

Emergency Alert Confirmation. See FIG. 15.

Press the green button to automatically call 911 and alert the local EMS about the event. If someone else is calling 911, or the local EMS have already been notified, press the purple button. If the user wishes to cancel the alert, press the blue button in the top right corner of the screen.

Start CPR. See FIG. 16.

If you are qualified to perform CPR, please begin to do so immediately. Once the responders arrive with the AED please press the green button in the middle to move on to the next screen. The user also has the option to cancel the alert for any reason by pressing the blue "cancel alert" button in the top right corner of the screen.

Attach AED. See FIG. 17.

When the responders arrive with the AED in hand, make sure to properly attach the device to the victim as quickly as possible. Once this has been completed press the green button in the middle of the screen to move on to the next step. If the user needs to cancel the alert, press the blue button in the top right corner.

Confirm EMS

Once EMS arrives at the scene press the green button in the middle to complete the alert.

Augmented Reality

Embodiments of the invention provide augmented reality displays to system users, for example to show a route to equipment, to a building exit, etc. To augment a display feature, a map is created for the facility, sensors are located on the map, and routes through the facility are established.

Figure 18:
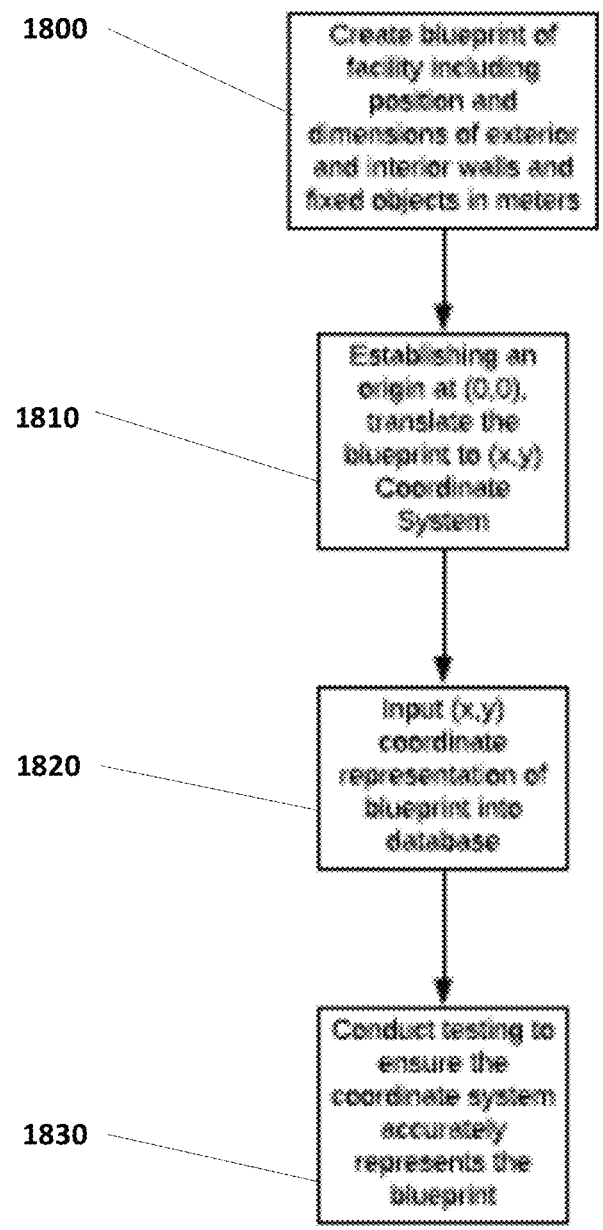
FIG. 18 is a flow diagram showing the creation of a digital representational map of a facility according to the invention.

Digital Representation Map of Facility (see FIG. 18). To create a digital representation map of a facility:

1. Creating or procuring an image, PDF, map, or other representation of the facility.

2. If an image or PDF, a software application traces the image into discernible vectors that permits the extraction of required data.
3. The software application extracts the dimensions of exterior walls, interior walls, and fixed objects, for example in meters or any other measurement scheme (1800).
4. Using an origin, for example at (0,0), the software application translates the extracted data to an coordinate system, such as an (x,y) coordinate system (1810).
5. The software application inputs appropriate coordinate system data into a database (1820).
6. Testing is performed to ensure that the coordinate system is accurate (1830).

Figure 19:
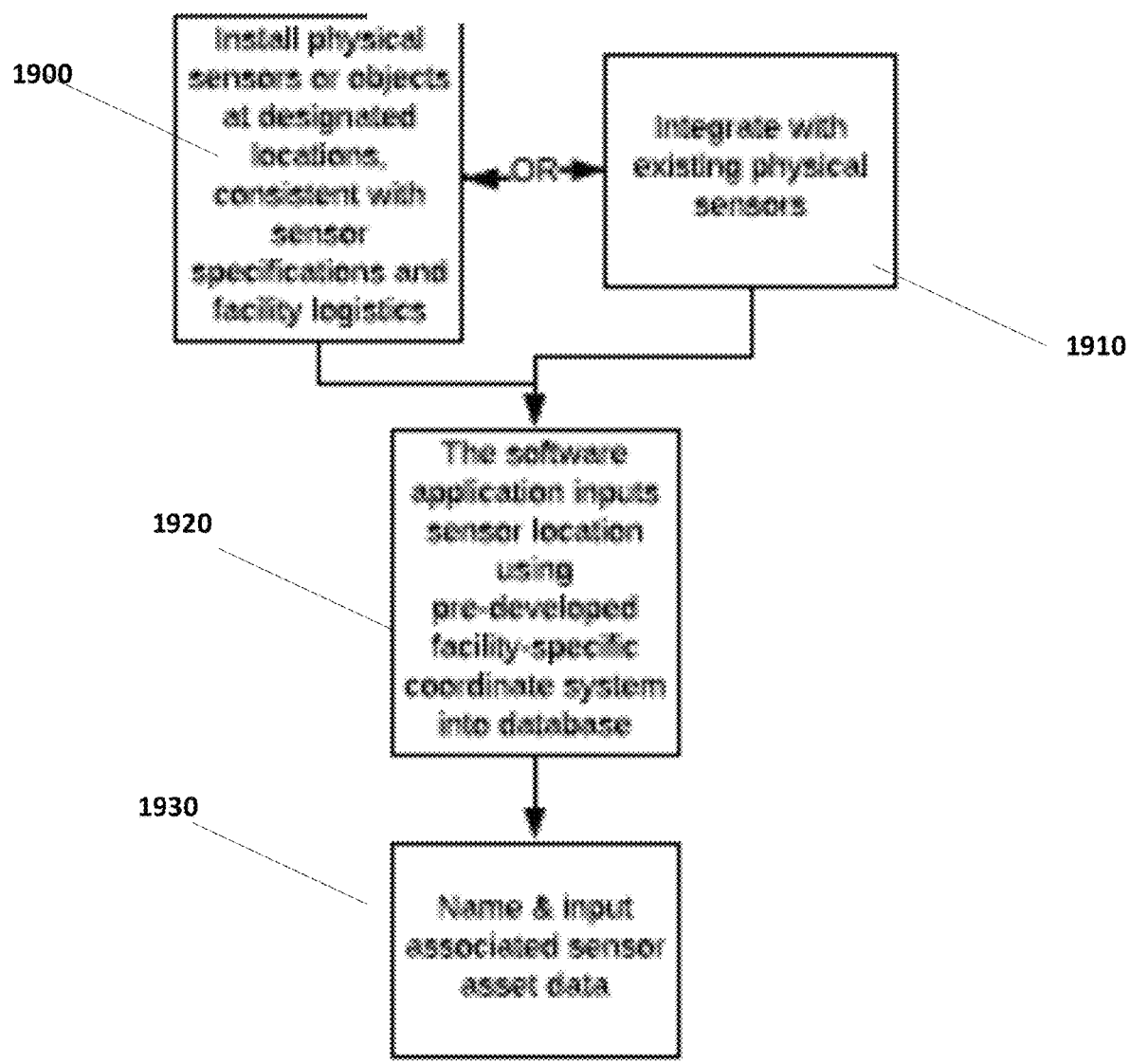
FIG. 19 is a flow diagram showing the installation or integration of the system with physical sensors according to the invention.

Install or Integrate with physical sensors, objects (see FIG. 19):
1. Install physical sensors of objects in or around the facility at designated locations, consistent with the sensor specifications and facility logistics (1900). For example, embodiments map the routes programmatically using a physical reference point, such as a seat number, QR code on exit signs, etc. Alternatively, integrate with existing physical sensors and/or physical objects (1910). For example, using Wi-Fi points, cell propagation antennas, Bluetooth, cell towers, etc.
2. The software application inputs sensor location that is determined using a pre-developed facility-specific coordinate system into the database (1920).
3. The software application allows the naming and input of associated sensor asset and/or marker data into the database (1930).

Establish horizontal and vertical planes (see FIG. 20):
The software application allows the user to enter a configuration mode and then scan the facility to establish horizontal and vertical planes attached to floors, walls, and fixed objects (2000).

Figure 21:
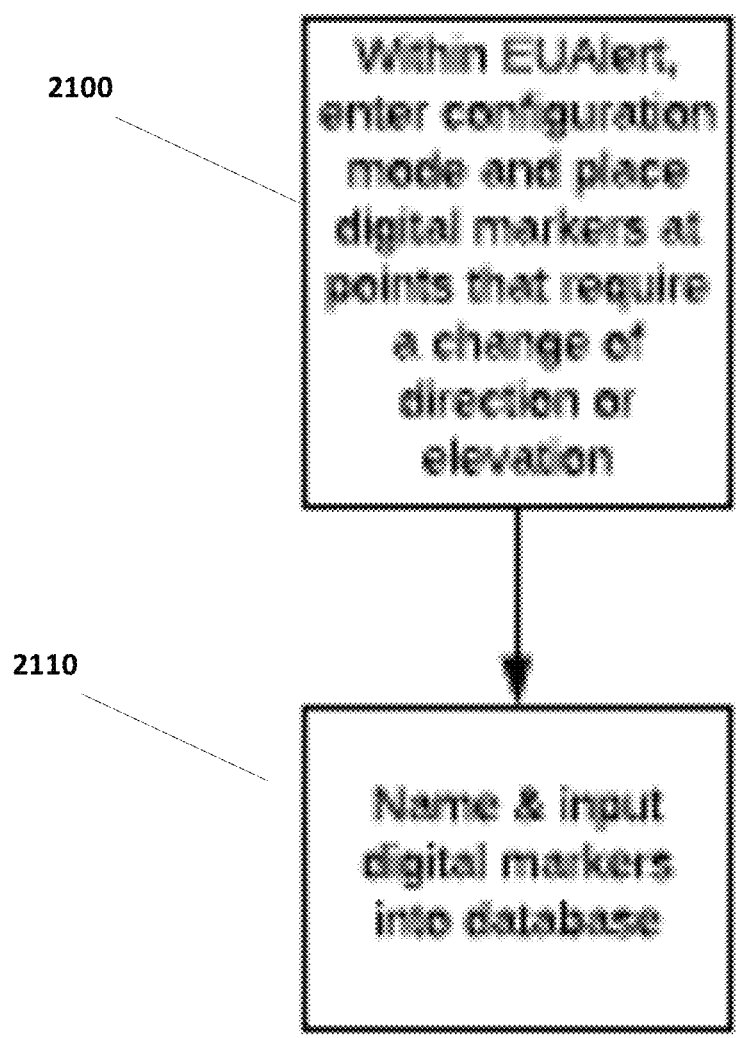
FIG. 21 is a flow diagram showing the placement of digital markers according to the invention.

Placement of digital markers (see FIG. 21):
1. The software application allows the user to enter configuration mode and then place digital markers at various points, such as reference points and/or those that require a change of direction, an elevator, or that are an end-point in a route (2100).
2. The software application allows the naming and input of digital markers into the database (2110).

Figure 22:
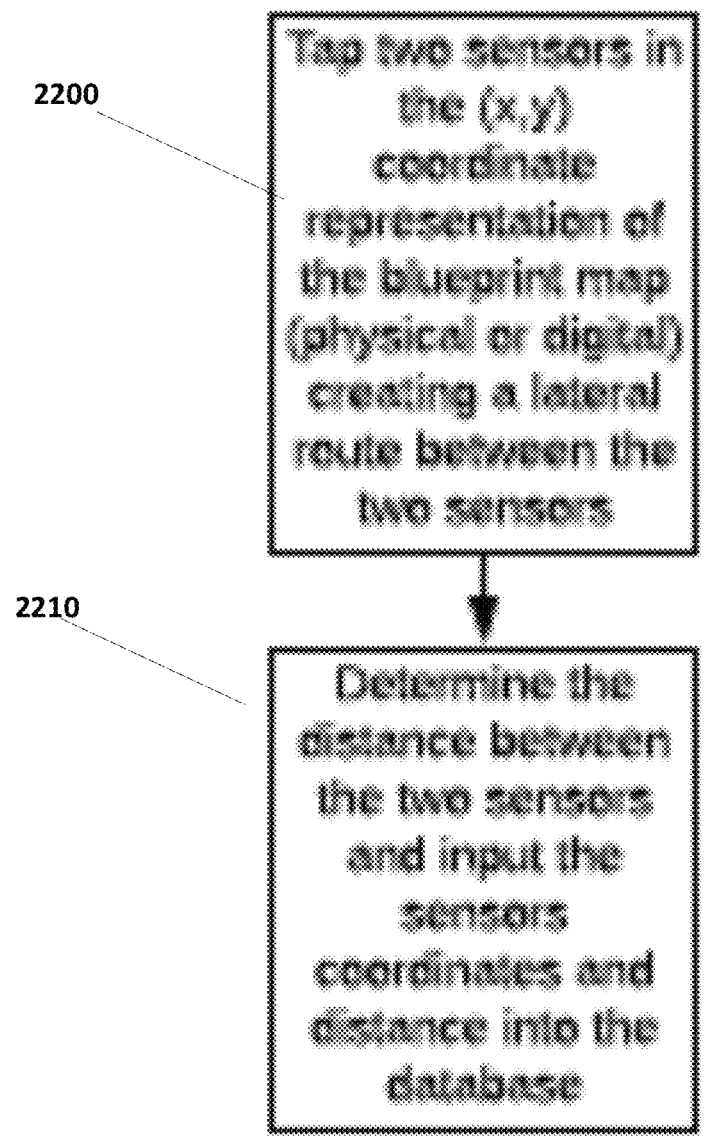
FIG. 22 is a flow diagram showing the defining of routes according to the invention.

Defining routes (see FIG. 22):
1. The software application allows a user to create a route between two or more selected physical sensors, objects, or digital markers by tapping on them on a display, thus creating a route between the two sensors, objects or digital markers (2200).
2. In embodiments, the software application determines the distance between two sensors and then inputs the sensors' coordinates and distance into the database. (2210)

Figure 23A:
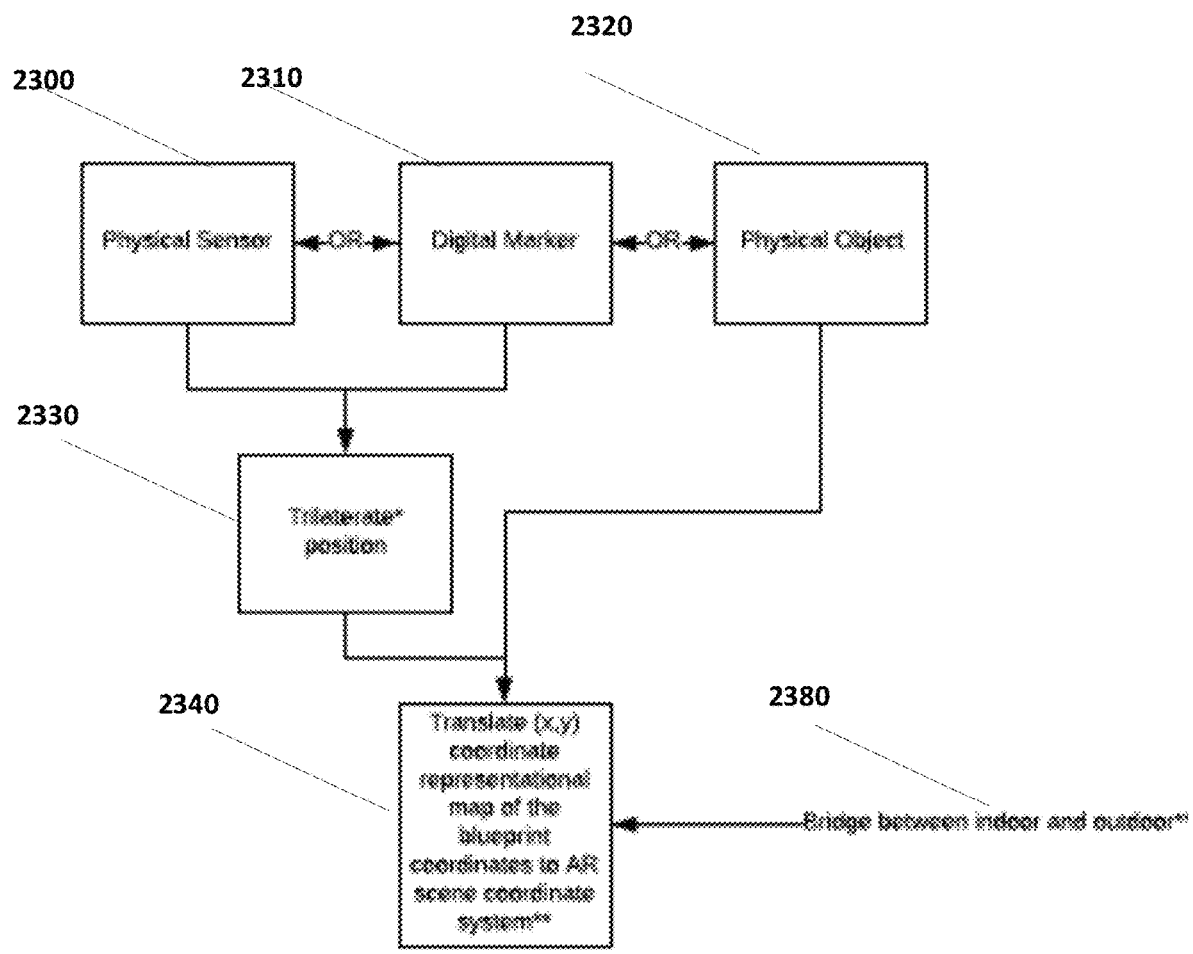
FIG. 23A is a flow diagram showing the indoor localization of a person or object according to the invention.
Figure 23B:
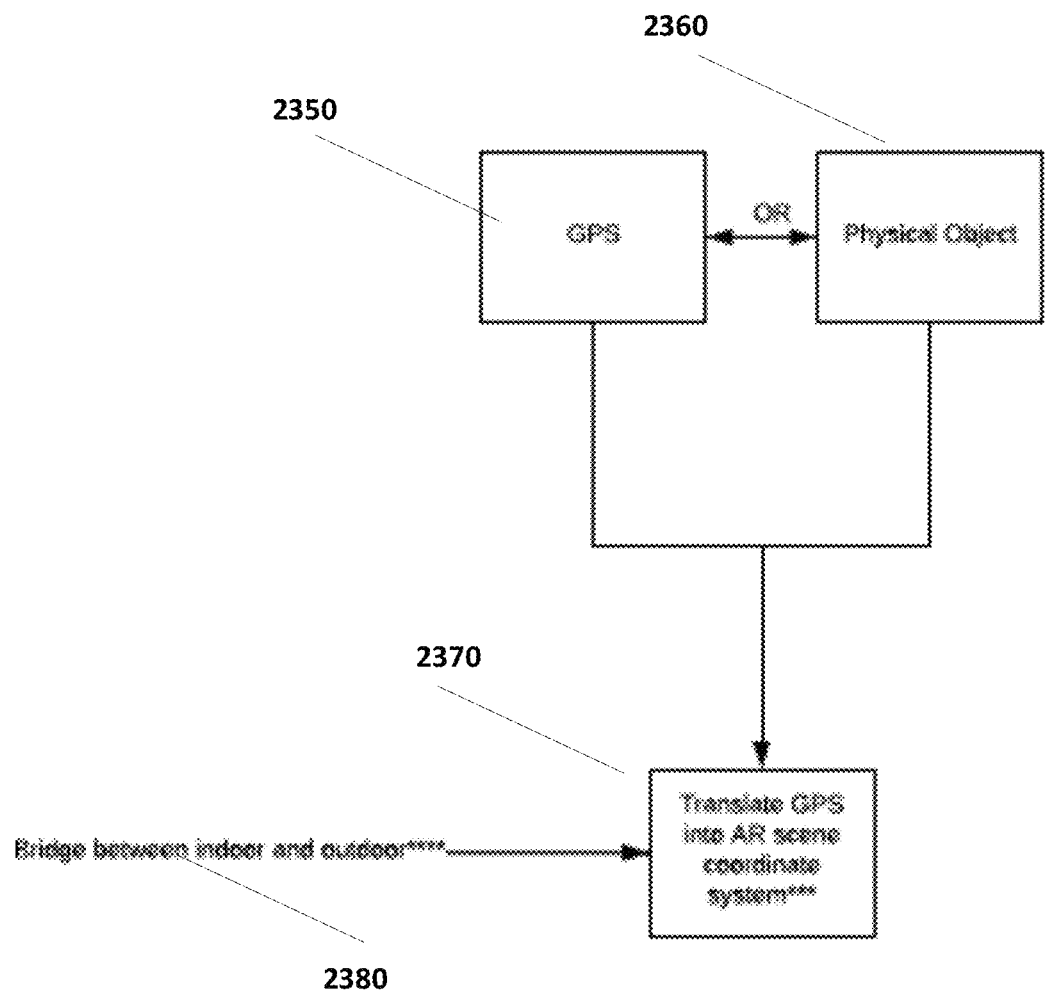
FIG. 23B is a flow diagram showing the outdoor localization of a person or object according to the invention.

Indoor localization of Person or Object (see FIG. 23A):
1. In embodiments, the software application uses a combination of three physical sensors (2300), digital markers (2310), or physical object locations (2320) to triangulate the position of a person or object to be routed from or to.
2. The software application determines the distance to the sensors, for example using the sensor's frequency and power information.
3. In embodiments, the distance is then used by the software application to triangulate the position of a person or object (2330). If a physical sensor is used, e.g. BLE Beacons; otherwise, if a digital marker is used, the indoor location is inherently given.
4. The coordinate of the triangulated position is translated by the software application from the (x,y) coordinate system to the augmented reality scene coordinate system (2340).
5. If the user moves from an indoor location to an outdoor location, the outdoor localizing is used (2380) (see FIG. 23B).

Outdoor localization of Person or Object (see FIG. 23B):
1. The software application uses, for example, GPS data gathered from the phone's hardware (2350) or physical object location (2360) to determine the position of the person or object
2. The location is translated by the software application into the augmented reality scene coordinate system (2370).

Figure 24:
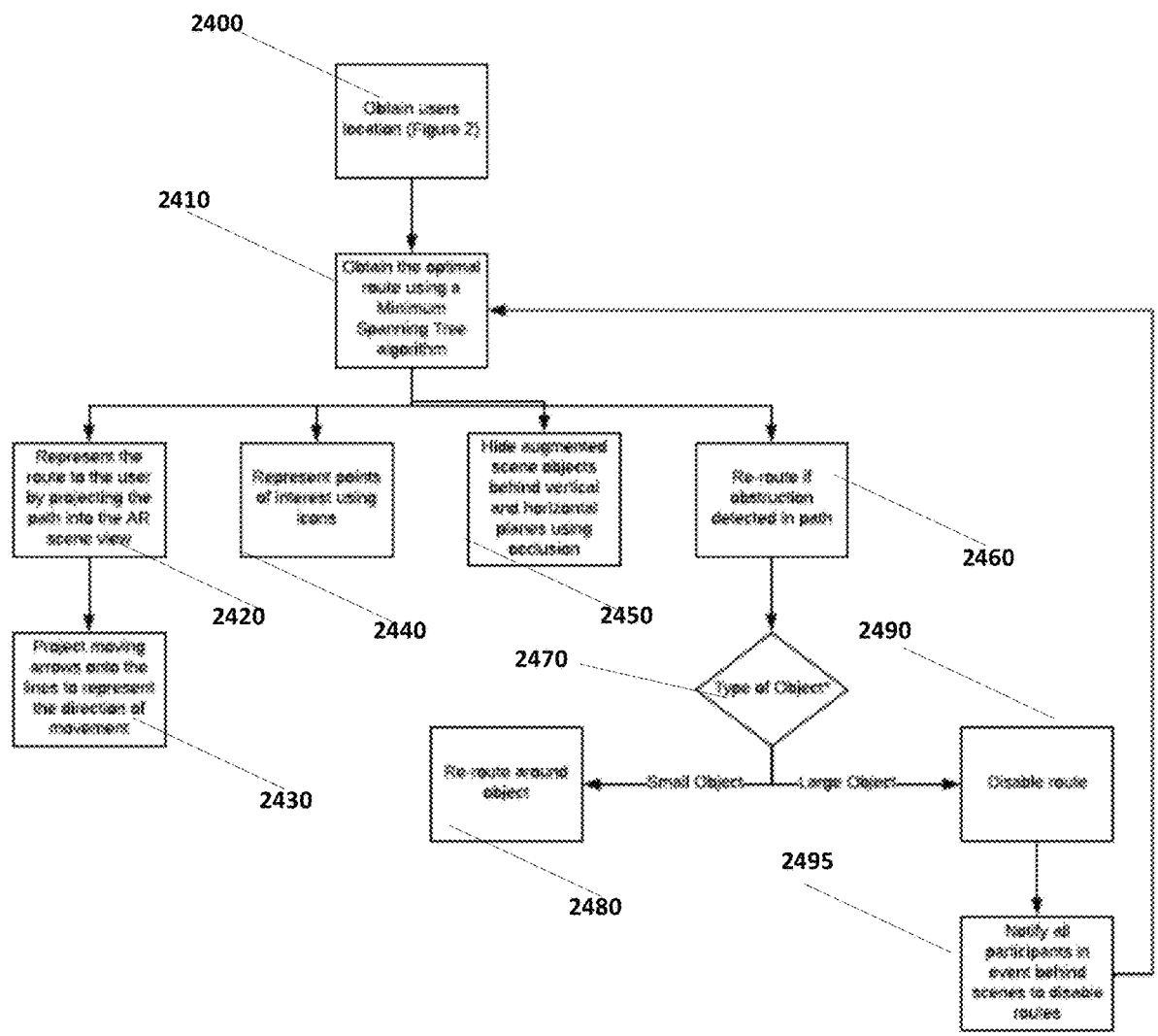
FIG. 24 is a flow diagram showing routing according to the invention.

Routing (see FIG. 24):
1. After the user's location is obtained (2400) (see FIGS. 23A/23B), the software application uses a Minimum Spanning Tree algorithm or other method for determining the quickest route given coordinates to obtain the optimal route (2410).
2. The software application:
a. Represents the route to the user by projecting the path into the augmented reality scene view (2420).
b. Represents the movement by projecting arrows onto the lines (2430).
c. Represents points of interest using icons (2440).
d. Hides augmented scene objects behind vertical and horizontal planes, for example, using a transparent mask that is overlayed on top of detected planes (2450).
e. Re-routes the user if an obstruction is detected in the path (2460), the type of object is identified (2470):
 i. Small objects: Re-route around the object (2480); and
 ii. Large objects: Disable route (2490).
  Notify all participants in the event to disable the blocked route (2495); and
  As part of the notification, machine learning is used by the software application to determine the type of obstruction, e.g. desk, fire, collapsed wall.

AR Workflow

Embodiments of the invention provide an augmented reality app in a mobile or wearable device that uses multiple sensing methods to position a user inside or outside a building. Based on the user's location, the app superimposes a route into an augmented scene, thus routing the user from their location to a calculated point of interest. Based on new information from various sensing methods, the application responds by directing the user towards a different route if their primary route becomes compromised. The new route information is immediately transmitted to other nearby users to be re-routed as necessary.

Sensing devices (mobile or wearable) are defined to be any handheld or wearable devices that are capable of displaying a 2D or 3D rasterized map or augmented scene, such as:
Mobile Cellphone
Smart Watch
Smart Glasses
Tablets
Laptops The aforementioned devices are used based on available positioning sensors.

The augmented reality app uses at least one of the following sensing methods to achieve indoor positioning:
1. Passive Sensing: Scan a QR code, bar code, or object of interest with camera
2. Lidar 3. Active Sensing: RF Beacons, BLE Beacons, Cellular propagation antennas, WI-FI access points, Emergency Lights, Bluetooth Sensing is not limited to those techniques listed above. Additionally, as new methods are created embodiments of the invention can use such methods for user positioning.

Process

Using a sensing device, a user opens the app and the app begins collecting data to attempt to triangulate the user's position, if available:
  GPS coordinates (longitude, latitude, altitude)
  Active sensor information
  Etc.

Exemplary Triangulation Formula

If active sensors are being used, a triangulation formula is applied to the three nearest sensors:

Part I—Obtain a translation vector and angle

1. Use the three closest beacons by determining their distance:

$$D = 10 \frac{T_x - R_s}{10n} \quad \text{(Eq. 1)}$$

Where $T_x$=given TxPower of the sensor,
$R_s$=RSSI value of the sensor,
n=2, though can be calibrated between 2-4

2. Create a translation vector by using $P_1$ and moving $P_1$ to the origin, therefor the translation vector is:

$$\vec{V_1} = -P_1 \quad \text{(Eq. 2)}$$

3. Apply the translation vector to $P_1$, $P_2$, $P_3$ $$P_1 = P_1 + \vec{V_1} \quad \text{(Eq. 3)}$$

$$P_2 = P_2 + \vec{V_1} \quad \text{(Eq. 4)}$$

$$P_3 = P_3 + \vec{V_1} \quad \text{(Eq. 5)}$$

4. Create a translation angle by moving $P_2 y$ to 0, thus creating a vector for $P_2 = \langle \langle P_2 \, x, 0 \rangle$:
  a. Find the magnitude of $P_2$ $$\|P_2\| = \sqrt{P_2 x^2 + y x^2} \quad \text{(Eq. 6)}$$

b. Obtain the angle $$\theta = \cos^{-1} \frac{P_2 \, x}{\|P_2\|} \quad \text{(Eq. 7)}$$

5. Apply the translation angle to $P_2$, $P_3$. Note $P_1 = \langle 0.0 \rangle$ so it does not need a translation angle applied to it
if $\theta > 0$, then use:

$$x = \cos\theta - \sin\theta \quad \text{(Eq. 8)}$$

$$y = \sin\theta + \cos\theta \quad \text{(Eq. 9)}$$

else if $\theta < 0$ $$x = \cos\theta + \sin\theta \quad \text{(Eq. 10)}$$

$$y = -\sin\theta + \cos\theta \quad \text{(Eq. 11)}$$

Part II—Calculate the Translated Triangulated Position $$x = \frac{r_1^2 - r_2^2 + P2_x^2}{2P2_x} \quad \text{(Eq. 12)}$$

$$y = \frac{r_1^2 - r_3^2 + P3_x^2 + P3_y^2}{2P3_y - \frac{P3_x}{P3_y}x} \quad \text{(Eq. 13)}$$

where $r_n$=radius (distance) of n beacon,
$P_n$=translated beacon X, Y coordinate
let $\vec{V_1} = \langle x, y \rangle$ Part III—Translate $\vec{v}$ to the Original Rotation and Translation 1. Rotate the position of $\vec{v}$ by $-\theta$ using the formula defined in Part I.5 above 2. Translate $\vec{v}$ by $\vec{v} = \vec{v} - \vec{V_1}$ Note: the sensors location is pre-determined and mapped into a coordinate system that, in an embodiment, is defined in meters by the facilities dimensions.

Otherwise, if passive sensors are being used, the user scans an object with a camera or other mechanism:

$\vec{v}$ =position of passive mechanism $\vec{v}$ is an X,Y coordinate, expressed in meter and based in the facility that is used to determine the user's location. The coordinates are checked against the user's device accelerometer and gyroscope to ensure accurate readings.

Given an accurate location reading, a minimum-spanning-tree algorithm, for example, is used to calculate a route from the users' physical location, augmented into the coordinate system, to a point of interest, e.g. another user's phone, physical object (equipment), point of interest such as GPS, non-GPS.

The route is determined, for example, by using minimum values between a tree of points. Points themselves are defined to be coordinates in the augmented map, as determined by digital markers, GPS markers, or physical sensors, e.g. BLE beacons.

Once a refined route has been determined, the route is augmented into:

1. A map of the facility, such as a 2D rasterized map or other representation of the facility or outdoor location:
  In an embodiment, to determine a 2D rasterized map, a set of coordinates determining exterior and interior walls are required. The information is then uploaded into the system. The rasterized map is a representation of connecting the coordinates together.
  Outdoor location is defined by any available technique, such as a GPS coordinate, obtained by the phone's mechanism/API, etc.

2. The Augmented Reality scene:
  The scene position of the line is calculated from the digital markers defining the routes. In embodiments, the scene-position of a line representing the route is calculated and translated from the 2D coordinate system into a 3D scene coordinate system.
  The line representation consists of moving arrows from the direction of the users position to the point of interest. If there are markers delineating exit points, corners, obstructions, the line, and thus the arrows, move towards the next closest marker.
  Markers indicating, for example, point of interests are displayed above the specified point of interest at a predetermined height; such points of interest include but are not limited to, e.g. another user's phone/ distress, equipment, assembly area, etc.

Objects behind stationary objects are omitted, for example, by using occlusion behind detected vertical and horizontal planes. The route does not appear through walls, doors, large objects, such as tables, desks, couches, etc.

As a user follows the route and an obstruction is detected:
Small obstruction (chair): a minor correction is calculated around the small object, if possible.
Large obstruction (fire, collapsed wall): the route is disabled and a new route using an alternative path is calculated. Nearby devices are updated of the newly disabled route.

Setting Up

A configuration process from a client-side or system-side administrator is required to predetermine points of interest when digital markers are used.

Figure 25:
FIGS. 25 and 26 show the placing of markers in connection with AR-based routing within or about a facility.
Figure 26:
Figure 27:
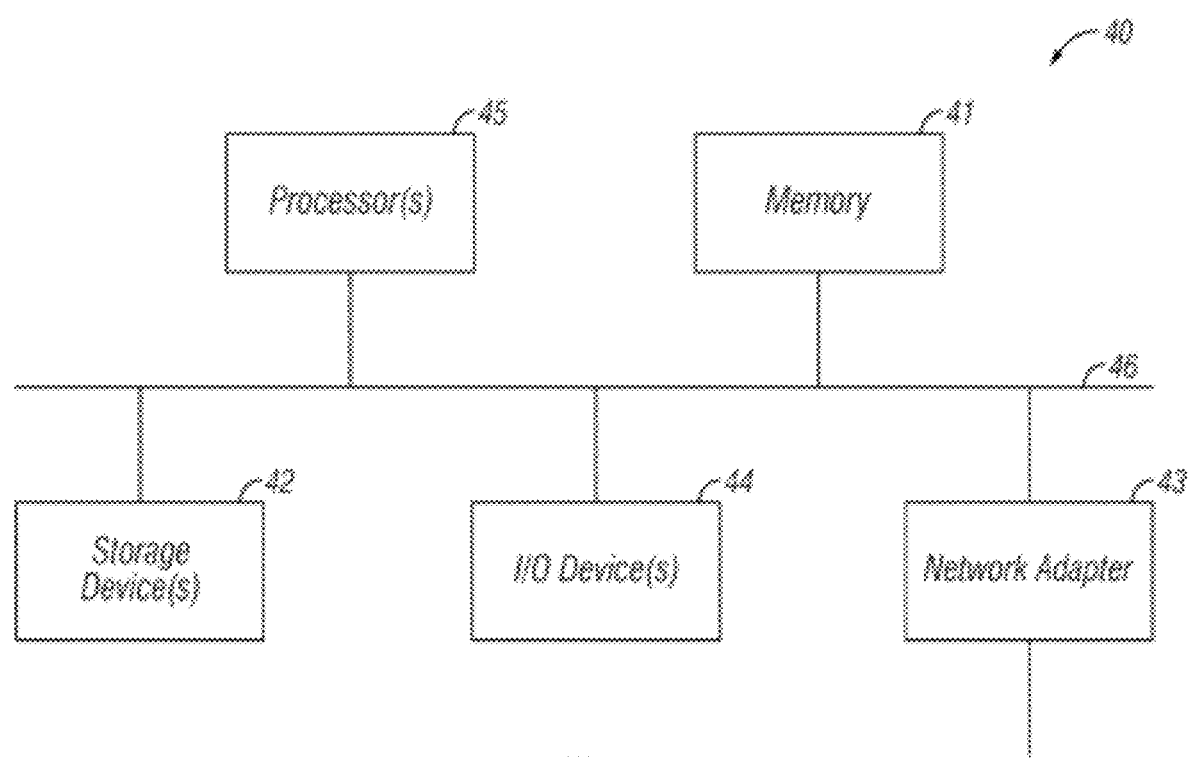
FIG. 27 is a block schematic diagram showing a machine in the example form of a computer system within which a set of instructions for causing the machine to perform one or more of the methodologies discussed herein may be executed.

Using a configuration applet, several things must be set up:
1. Set up the map by providing a digital copy of the blueprint. Alternatively, translate physical dimensions of the user's location into a desired coordinate system, e.g. measured in meters or any other desired measurement system.
2. Placement of physical sensors, e.g. BLE Beacons; scannable indicators, e.g. barcodes, QR codes; or other methods of indoor-positioning. The location must be tracked in the system.
3. Placement of physical sensors or digital markers on equipment storage housing or the equipment itself. Markers also include, for example, dynamic sensors, e.g. handheld devices, wearables, such as glasses and gloves, watches, computers, phones, etc. These sensors track where the equipment is stored so the location can be used for routing.
4. Identifying stationary and permanent objects, such as flooring, walls, tables, desks, etc. to determine vertical and horizontal planes that are used for occlusion.
5. Identifying points of interest at changes-of-directions in the route, e.g. corners, bottom of stairwell, top of stairwell. Embodiments use physical sensors for equipment or digital markers for this purpose, although digital markers remain stationary and do not move with the equipment. FIGS. 25 and 26 show the placing of markers in connection with AR-based routing within or about a facility during a distress event (FIG. 25) and an evacuation (FIG. 26).
6. Configuration of an easily-recognizable naming convention for the markers, sensors, and equipment. Namable objects are set in either a list view of all placed markers, sensors, or via the map.
7. Embodiments create routes by any method of associating one sensor with another. In an embodiment, configuration of the route is set up in the map by opening the map and selecting two markers, e.g. digital, GPS, physical sensor. Once two markers are selected, the app automatically creates a route between the two points and represents the route with a line on the 2D rasterized map between the two points.

At any time or once the configuration is complete, the configuration can be saved or updated. When saved or updated, the newly added or changed information is uploaded to the secure server for all users to have access to while using the application.

When a user opens the application, the server is queried based on the user's chosen static location and physical location, as determined by GPS, as well as relative distance to predetermined facilities. The configuration for those predetermined facilities is used in the processing and displaying of routes.

Use Cases

Embodiments of the invention use the augmented reality functionality to:
1. Direct workforce personnel during evacuations, leading them to pre-designated routes, including the designated floor exit, building exit, and to their assembly point.
2. Direct workforce personnel to designated shelters in their facility.
3. Direct responders to ill or injured personnel who have used the app to indicate they are ill or in distress.
4. Direct responders to the nearest functioning emergency equipment, including AEDs, disaster bags, emergency medical kits, fire extinguishers, etc.
5. Direct all personnel away from hazards or danger zones resulting from the ongoing emergency. For example, if the roof caves over the rear evacuation exit, the herein disclosed AR automatically re-routes them toward a safe exit.
6. Direct all personnel away from dynamic danger zones, such as an active shooter moving through a building.
7. Administrators draw danger zones corresponding with unsafe areas that the herein disclosed AR sees as unavailable routes and optimizes the user's route to safety.
8. The app allows all personnel to attach photos of suspicious activity and persons. The admin can re-localize the danger zone as, for example, the shooter's location changes, directing personnel away from the dynamic danger zone.
9. Use AR, nodes or sensors to track individual personnel's location automatically indoors and outdoors, including exiting floor, exiting building, and arriving at assembly points.
10. Define one or more digital markers, each of the digital markers comprising a set of coordinates that define an interim point of interest. Use a relational algorithm and coordinate system to create one or more routes with said digital markers. Where the digital markers are a set of coordinates captured by an imaging device for an augmented reality scene.
11. Use machine learning to automatically detect obstructions and capture, track, and report dangers and occluded routes.
12. Provide redundant communication mechanisms, such as Bluetooth, to communicate data between personnel when cellular, Internet connectivity, and/or Wi-Fi is unavailable.

Computer Implementation

FIG. 18 is a block diagram of a computer system that may be used to implement certain features of some of the embodiments of the invention. The computer system may be a server computer, a client computer, a personal computer (PC), a user device, a tablet PC, a laptop computer, a personal digital assistant (PDA), a cellular telephone, an iPhone, an iPad, a Blackberry, a processor, a telephone, a Web appliance, a network router, switch or bridge, a console, a hand-held console, a (hand-held) gaming device, a music player, any portable, mobile, hand-held device, wearable device, or any machine capable of executing a set of instructions, sequential or otherwise, that specify actions to be taken by that machine.

The computing system 40 may include one or more central processing units ("processors") 45, memory 41, input/output devices 44, e.g. keyboard and pointing devices, touch devices, display devices, storage devices 42, e.g. disk drives, and network adapters 43, e.g. network interfaces, that are connected to an interconnect 46.

In FIG. 18, the interconnect is illustrated as an abstraction that represents any one or more separate physical buses, point-to-point connections, or both connected by appropriate bridges, adapters, or controllers. The interconnect, therefore, may include, for example a system bus, a peripheral component interconnect (PCI) bus or PCI-Express bus, a Hyper Transport or industry standard architecture (ISA) bus, a small computer system interface (SCSI) bus, a universal serial bus (USB), IIC (12C) bus, or an Institute of Electrical and Electronics Engineers (IEEE) standard 1394 bus, also referred to as Firewire.

The memory 41 and storage devices 42 are computer-readable storage media that may store instructions that implement at least portions of the various embodiments of the invention. In addition, the data structures and message structures may be stored or transmitted via a data transmission medium, e.g. a signal on a communications link. Various communications links may be used, e.g. the Internet, a local area network, a wide area network, or a point-to-point dial-up connection. Thus, computer readable media can include computer-readable storage media, e.g. non-transitory media, and computer-readable transmission media.

The instructions stored in memory 41 can be implemented as software and/or firmware to program one or more processors to carry out the actions described above. In some embodiments of the invention, such software or firmware may be initially provided to the processing system 40 by downloading it from a remote system through the computing system, e.g. via the network adapter 43.

The various embodiments of the invention introduced herein can be implemented by, for example, programmable circuitry, e.g. one or more microprocessors, programmed with software and/or firmware, entirely in special-purpose hardwired, i.e. non-programmable, circuitry, or in a combination of such forms. Special-purpose hardwired circuitry may be in the form of, for example, one or more ASICs, PLDs, FPGAs, etc.

Although the invention is described herein with reference to the preferred embodiment, one skilled in the art will readily appreciate that other applications may be substituted for those set forth herein without departing from the spirit and scope of the present invention.

For example, embodiments of the invention apply rules to identify the operational status of emergency equipment based on identifying parameters, including most recent successful maintenance inspection, most recent confirmation of GPS location, expiration date of AED pads, expiration date of AED batteries, other expiration dates checked in case of other equipment. See U.S. provisional patent application Ser. No. 61/892,836, filed October 18, 23, which application is incorporated herein in its entirety by this reference thereto.

Accordingly, the invention should only be limited by the Claims included below.

The invention claimed is:

1. A computer implemented method for routing communications signals in response to an emergency, comprising:
providing a processor for receiving an input signal comprising an initial notification transmitted by a bystander at a location and indicating that there is an emergency at said location;
independently of a central emergency medical services (EMS) notification system, said processor extracting content from said signal comprising identification of a specific location of said emergency and identification of said emergency type;
said processor using said extracted content to identify laypersons at or near said location who are trained responders for said emergency and who are most qualified to respond to said emergency based upon the type of said emergency;
said processor prioritizing said identified most qualified trained responders based upon their training and qualification; and
independently of said central notification system, said processor transmitting a prioritized alert directly to at least said identified most qualified trained responders comprising said emergency type and said emergency location;
said alert further comprising the display of a dynamic map identifying and displaying any of the location of any of work force personnel, trained responders, emergency equipment, exit doors, and visual dynamic directions to a nearest exit.

2. The method of claim 1, further comprising generating said dynamic map by:
creating a map for said location to augment a display feature;
locating sensors and/or physical objects on said map, and establishing routes to or away from said emergency location.

3. The method of claim 2, further comprising creating said map for said location by:
procuring an image, file, map, or other representation of all or part of a facility;
when an image or file is procured tracing said image into discernible vectors for extraction of required data;
extracting dimensions at said location of exterior walls, interior walls, and fixed objects;
translating said extracted dimensions to a representative coordinate system; and
inputting said representative coordinate system data into a database.

4. The method of claim 3, further comprising installing or Integrating said sensors or physical objects by:
installing physical sensors or objects in or around said location at designated positions; and/or
integrating with existing physical sensors and/or physical objects.

5. The method of claim 3, further comprising;
inputting one or more sensor locations into said database;
establishing horizontal and vertical planes attached to floors, walls, and fixed objects at said location; and
placing digital markers at points divergent points, including points that require a change of direction, an elevator, or that are an end-point in a route.

6. The method of claim 5, further comprising:
creating a route between two selected physical sensors, objects, or digital markers;
determining distance between the two selected physical sensors, objects, or digital markers; and
inputting said selected physical sensors, objects, or digital markers s' coordinates and distance into said database.

7. The method of claim 6, further comprising localizing an indoor person or object by:
using a combination of physical sensors, digital markers, or physical object locations to triangulate a position of a person or object to be routed from or to;
determining distance to the sensors;

using distance to triangulate the position of a person or object;

translating coordinates of the triangulated position to an augmented reality scene coordinate system; and when the user moves from an indoor location to an outdoor location, switching to outdoor localizing.

8. The method of claim 6, further comprising localizing any of an outdoor person, object, or shape by:

using location data gathered from a user device or physical object location to determine a location of the person or object;

translating said location into an augmented reality scene coordinate system; and when the user moves from an outdoor location to an indoor location, switching to indoor localizing.

9. The method of claim 6, further comprising:

using a minimum spanning tree algorithm after the user's location is obtained to obtain an optimal route.

10. The method of claim 6, further comprising:

representing the route to the user by projecting a path into the augmented reality scene view;

representing movement by projecting arrows onto the path;

representing points of interest using icons;

hiding augmented scene objects behind a physical object;

re-routing the user if an obstruction is detected in the path by:

identifying a type of object:

for small objects, re-routing around the object; and for large objects, disabling the route;

notifying all participants in the event of a disabled or blocked route; and using machine learning to determine the type of obstruction.

11. The method of claim 1, further comprising:

displaying said dynamic map using multiple sensing methods to position a user inside or outside of a facility;

based on the user's location, superimposing a route into an augmented scene to route the user from a current location to a calculated point of interest; and based on new information from one or more sensing methods, directing the user towards a different route if their primary route becomes compromised;

wherein the new route information is immediately transmitted to nearby users to be re-routed as necessary.

12. A computer implemented method for routing communications signals in response to an emergency, comprising:

providing a processor for receiving an input signal comprising an initial notification transmitted by a bystander at a location and indicating that there is an emergency at said location;

independently of a central emergency medical services (EMS) notification system, said processor extracting content from said signal comprising identification of a specific location of said emergency and identification of said emergency type;

said processor using said extracted content to identify laypersons at or near said location who are trained responders for said emergency and who are most qualified to respond to said emergency based upon the type of said emergency;

said processor prioritizing said identified most qualified trained responders based upon their training and qualification; and independently of said central notification system, said processor transmitting a prioritized alert directly to at least said identified most qualified trained responders comprising said emergency type and said emergency location;

said alert further comprising the display of a dynamic map identifying and displaying any of the location of any of work force personnel, trained responders, emergency equipment, exit doors, and visual dynamic directions to a nearest exit.

13. The method of claim 12, further comprising:

said processor identifying location and operational status of emergency equipment based on parameters that include any of most recent successful maintenance inspection, expiration dates that are relevant to critical equipment, components, supplies, and medication that require routine replacement due to their age and/or expiration date; and said processor providing notifications to trained responders who have indicated that they are responding, said notifications identifying nearest appropriate emergency equipment.

14. The method of claim 12, further comprising:

when GPS is available, said processor using emergency event GPS location and dynamically comparing said emergency event GPS location with a closest location as determined by GPS to identify appropriate trained responders; and when GPS is not available said processor using pre-configured location data.

15. The method of claim 12, further comprising:

said processor identifying location and operational status of emergency equipment based on parameters that include most recent confirmation of GPS location.

16. The method of claim 12, further comprising:

said processor receiving a confirming response from trained responders who respond to said alert; and said processor providing a notification to said bystander indicating receipt of said notification from said trained responders who respond to said alert.

17. The method of claim 12, further comprising:

said processor using multiple real-time notification channels to immediately communicate between said bystander and said responder.

18. The method of claim 12, further comprising:

responsive to any of said initial notification and said content, said processor providing said bystander with any of specific text-based, graphic, video, and voice instructions on actions to perform in response to said emergency.

19. The method of claim 12, further comprising:

said processor providing communication and activity tracking of all communications and times at which actions are taken.

20. The method of claim 12, further comprising:

said processor receiving GPS location information for emergency equipment and confirmation that said emergency equipment is operational.

21. The method of claim 12, further comprising:

said emergency comprising a sudden cardiac arrest (SCA); and any of said processor using geo-location to identify said trained responders based on their location when providing said confirming response;

said processor providing identification of AEDs based upon proximity and operational readiness;

said processor providing notifications to said trained responders identifying a nearest AEDs prioritized by proximity; and said processor providing communication and activity tracking of any of time a responder arrived, if and when an AEC is attached, and when an EMS arrived.

22. The method of claim 12, further comprising:
said processor communicating instructions to individuals based on any of a type of emergency, organizational structure, pre-defined roles, equipment availability, training and experience, and an organization's emergency policies, procedures, protocols, and emergency response plans.

23. The method of claim 12, further comprising:
using AR, nodes or sensors to track individual personnel's location automatically indoors and outdoors, including exiting floor, exiting building, and arriving at assembly points.

24. The method of claim 12, further comprising:
defining one or more digital markers, each of said digital markers comprising a set of coordinates that define an interim point of interest; and
using a relational algorithm and coordinate system to create one or more routes with said digital markers.

25. The method of claim 24, further comprising:
said digital markers comprising a set of coordinates captured by an imaging device for an augmented reality scene.

26. The method of claim 12, further comprising:
using machine learning to automatically detect obstructions and capture, track, and report dangers and occluded routes.

27. The method of claim 12, further comprising:
providing redundant communication mechanisms to communicate data between personnel when cellular, Internet connectivity, and/or Wi-Fi is unavailable.

28. A computer implemented method for routing communications signals in response to an emergency, comprising:
providing a processor for receiving an input signal comprising an initial notification transmitted by a bystander at a location and indicating that there is an emergency at said location;
independently of a central emergency medical services (EMS) notification system, said processor extracting content from said signal comprising identification of a specific location of said emergency and identification of said emergency type;
said processor exchanging information with individual workforce members comprising any of notification to evacuate, where to evacuate to, confirmation of receipt of notification by workforce, evacuation from building confirmation, arrival at assembly point confirmation, notification of an emergency, and notification of individual workforce members who have issued a distress notification;
independently of said central notification system, said processor transmitting an alert directly to said individual workforce members
comprising the display of a dynamic map identifying and displaying any of the location of any of work force personnel, trained responders, emergency equipment, exit doors, and visual dynamic directions to a nearest exit.

29. The method of claim 28, further comprising:
said processor providing an incident commander with aggregate, continually updated reports of individuals who have successfully evacuated by points of evacuation; receipt of notification, including GPS location; evacuation from building, with new GPS location; and arrival at an assembly point by GPS location.

30. The method of claim 28, further comprising:
said processor providing an incident commander with distress notifications from individual workforce members; and
said processor triaging said distress notifications to security and emergency response team members.

31. The method of claim 28, further comprising:
said processor providing an incident commander with aggregate, continually updated reports of distress notification by degree of triage assigned.

32. The method of claim 28, further comprising:
said processor providing any of coded or time-limited coded drills for designated responders, or classes and non-coded, facility wide drills to simulate actual emergencies.

33. The method of claim 28, further comprising:
said processor incorporating time-based prompts to ensure necessary individuals are notified, and necessary actions are timely performed.

34. The method of claim 28, further comprising:
said processor ascertaining whether a workforce member whose cell phone is turned on is still in a facility if said workforce member has not confirmed receipt of a notification.

35. The method of claim 28, further comprising:
said processor informing said bystander how many responders have been notified.

36. The method of claim 28, further comprising:
said processor identifying an individual having known disabilities, as specified during said individual's registration; and
said processor issuing a pre-configured distress signal during an evacuation with specific instructions for a trained responder, and location of nearest appropriate equipment based upon the disability, to assist said individual with equipment necessary to ensure they are able to evacuate said individual.

37. The method of claim 28, further comprising:
using AR, nodes or sensors to track individual personnel's location automatically indoors and outdoors, including exiting floor, exiting building, and arriving at assembly points.

38. The method of claim 28, further comprising:
defining one or more digital markers, each of said digital markers comprising a set of coordinates that define an interim point of interest; and
using a relational algorithm and coordinate system to create one or more routes with said digital markers.

39. The method of claim 38, further comprising:
said digital markers comprising a set of coordinates captured by an imaging device for an augmented reality scene.

40. The method of claim 28, further comprising:
using machine learning to automatically detect obstructions and capture, track, and report dangers and occluded routes.

41. The method of claim 28, further comprising:
providing redundant communication mechanisms to communicate data between personnel when cellular, Internet connectivity, and/or Wi-Fi is unavailable.

42. The method of claim 12, further comprising:
said dynamic map providing an augmented reality display for any of:
directing workforce personnel during evacuations and leading them to pre-designated routes, including a designated floor exit, building exit, and/or assembly point;

directing workforce personnel to designated shelters proximate to their location;

directing responders to ill or injured personnel who have indicated that they are ill or in distress;

directing responders to nearest functioning emergency equipment;

directing personnel away from hazards or danger zones resulting from an ongoing emergency;

directing personnel away from dynamic danger zones;

drawing danger zones corresponding with unsafe areas that are unavailable routes and optimizing the user's route to safety; and attaching photos of suspicious activity and persons.

43. The method of claim 28, further comprising:

said dynamic map providing an augmented reality display for any of:

directing workforce personnel during evacuations and leading them to pre-designated routes, including a designated floor exit, building exit, and/or assembly point;

directing workforce personnel to designated shelters proximate to their location;

directing responders to ill or injured personnel who have indicated that they are ill or in distress;

directing responders to nearest functioning emergency equipment;

directing personnel away from hazards or danger zones resulting from an ongoing emergency;

directing personnel away from dynamic danger zones;

drawing danger zones corresponding with unsafe areas that are unavailable routes and optimizing the user's route to safety; and attaching photos of suspicious activity and persons.

\* \* \* \* \*